US009119933B2

(12) United States Patent
Bedford et al.

(10) Patent No.: US 9,119,933 B2
(45) Date of Patent: Sep. 1, 2015

(54) RESPIRATORY SYSTEM

(75) Inventors: Jon Richard Bedford, Huddersfield (GB); Malcolm Graham James, Halifax (GB); Neil Anthony Kaye, Balmain East (AU); Jeno Kurja, Aerdenhout (NL); Rik Julia Raoul Langerock, Merelbeke (BE)

(73) Assignee: PLASTIFLEX GROUP, Paal-Beringen (BE)

( * ) Notice: Subject to any disclaimer, the term of this patent is extended or adjusted under 35 U.S.C. 154(b) by 1529 days.

(21) Appl. No.: 12/673,401

(22) PCT Filed: Aug. 14, 2008

(86) PCT No.: PCT/EP2008/060727
§ 371 (c)(1),
(2), (4) Date: Jan. 27, 2012

(87) PCT Pub. No.: WO2009/022004
PCT Pub. Date: Feb. 19, 2009

(65) Prior Publication Data
US 2012/0125333 A1  May 24, 2012

(30) Foreign Application Priority Data

Aug. 14, 2007 (EP) .................................... 07114350
Sep. 12, 2007 (EP) .................................... 07116251
Nov. 30, 2007 (EP) .................................... 07122033
Mar. 25, 2008 (EP) .................................... 08153243
Mar. 25, 2008 (EP) .................................... 08153245

(51) Int. Cl.
*A61M 16/06* (2006.01)
*A61M 16/10* (2006.01)
(Continued)

(52) U.S. Cl.
CPC ........... *A61M 16/1075* (2013.01); *A61M 16/06* (2013.01); *A61M 16/0816* (2013.01);
(Continued)

(58) Field of Classification Search
CPC . A61M 16/00; A61M 16/0069; A61M 16/08; A61M 16/1075; A61M 16/16; A61M 16/161; A61M 16/109; A61M 16/1095; A61M 16/162; A61M 16/202; A61M 15/00; A61M 16/0816; A61M 16/0875; A61M 16/10; A61M 16/108; A61M 16/142; A61M 16/06; G01F 1/684; G01F 1/6842; G01F 1/6888; G01F 1/688; G08B 21/16; G05B 9/03; A62B 9/00; A62B 23/02; A62B 7/00; B01D 53/268; B01D 47/00; B01D 53/26; G05D 22/02; G05D 9/03; G05D 22/00; F24F 3/14; F24F 3/12; G01N 27/223; G01N 33/0006; G01N 25/66; G01N 25/56; G01N 33/00; B01F 3/04; B29C 49/00; F16L 53/008; F24J 3/00; H05B 3/00; H05B 3/58
USPC ............. 128/200.24, 201.13, 203.12, 203.15, 128/203.17, 203.26, 203.27, 204.17, 128/204.18, 204.21; 239/338, 102.1, 102.2; 261/129, 154, DIG. 65; 122/4 A, 5.5, 122/7 B, 13.01, 13.3–19.2, 33, 487, DIG. 7
See application file for complete search history.

(56) References Cited

U.S. PATENT DOCUMENTS 2,073,335 A   3/1937  Connell
2,348,108 A   5/1944  Bulbulian
(Continued)

FOREIGN PATENT DOCUMENTS

DE   199 58 296 C1   9/2001
DE   100 21 783 A1   11/2001
(Continued)

*Primary Examiner* — Annette Dixon
(74) *Attorney, Agent, or Firm* — Sughrue Mion, PLLC

(57) ABSTRACT

A modular respiratory system to which different parts can be added in a convenient way enabling such upgraded respiratory system to deliver the most comfortable respiratory conditions at an acceptable cost of ownership.

9 Claims, 11 Drawing Sheets

(51) Int. Cl.
  *A61M 16/08* (2006.01)
  *A61M 16/16* (2006.01)
  *F16L 53/00* (2006.01)
  *H05B 3/58* (2006.01)
  *A61M 16/00* (2006.01)

(52) U.S. Cl.
  CPC ......... *A61M16/0875* (2013.01); *A61M 16/108* (2014.02); *A61M 16/109* (2014.02); *A61M 16/1095* (2014.02); *A61M 16/16* (2013.01); *A61M 16/161* (2014.02); *F16L 53/008* (2013.01); *H05B 3/58* (2013.01); A61M 2016/0027 (2013.01); A61M 2016/0039 (2013.01); A61M 2016/103 (2013.01); A61M 2016/1025 (2013.01); A61M 2205/3368 (2013.01); A61M 2205/3561 (2013.01); A61M 2205/3569 (2013.01); A61M 2205/3584 (2013.01); A61M 2205/3592 (2013.01); A61M 2205/3613 (2013.01); A61M 2205/3633 (2013.01); A61M 2205/3653 (2013.01); A61M 2205/502 (2013.01); H05B 2203/019 (2013.01); H05B 2203/02 (2013.01); Y10T 29/4998 (2015.01)

(56) References Cited

U.S. PATENT DOCUMENTS

| | | | |
|---|---|---|---|
| 2,591,992 | A | 4/1952 | Aerick |
| 3,028,290 | A | 4/1962 | Roberts et al. |
| 4,412,537 | A | 11/1983 | Tiger |
| 4,492,228 | A | 1/1985 | Makovic |
| 4,708,831 | A * | 11/1987 | Elsworth et al. ............. 261/130 |
| 4,905,686 | A | 3/1990 | Adams |
| 5,031,612 | A * | 7/1991 | Clementi ................. 128/204.14 |
| 6,039,696 | A | 3/2000 | Bell |
| 6,367,510 | B1 | 4/2002 | Carlson |
| 6,584,972 | B2 * | 7/2003 | McPhee ................... 128/203.17 |
| 7,051,733 | B2 * | 5/2006 | Gradon et al. ........... 128/203.17 |
| 7,114,497 | B2 * | 10/2006 | Aylsworth et al. |
| 8,235,041 | B2 * | 8/2012 | Seakins et al. ........... 128/204.14 |
| 2003/0059213 | A1 | 3/2003 | Mackie et al. |
| 2003/0183294 | A1 | 10/2003 | Carlson |
| 2006/0113690 | A1 * | 6/2006 | Huddart et al. ................ 261/129 |
| 2006/0144399 | A1 | 7/2006 | Davidowski et al. |
| 2006/0249160 | A1 | 11/2006 | Scarberry et al. |
| 2007/0265877 | A1 | 11/2007 | Rice et al. |
| 2008/0308100 | A1 * | 12/2008 | Pujol et al. ................ 128/203.14 |

FOREIGN PATENT DOCUMENTS

| | | |
|---|---|---|
| DE | 103 12 881 B3 | 5/2004 |
| DE | 10 2005 042 181 A1 | 4/2006 |
| DE | 10 2007 011 544 B3 | 6/2008 |
| EP | 1 138 341 A2 | 10/2001 |
| EP | 1 369 141 A1 | 12/2003 |
| EP | 1 741 462 A1 | 1/2007 |
| GB | 1 380 633 A | 1/1975 |
| GB | 2 431 359 A | 4/2007 |
| JP | 2005-261858 A | 9/2005 |
| WO | 96/20748 A1 | 7/1996 |
| WO | 97/47348 A1 | 2/1997 |
| WO | 97/10027 A1 | 3/1997 |
| WO | 97/18001 A1 | 5/1997 |
| WO | 00/76568 A1 | 12/2000 |
| WO | 2004/020031 A1 | 3/2004 |
| WO | 2004/039444 A1 | 5/2004 |
| WO | 2004/105846 A2 | 12/2004 |
| WO | 2005/011556 A2 | 2/2005 |
| WO | 2006019323 A1 | 2/2006 |
| WO | 2007/012140 A1 | 2/2007 |
| WO | 2007051230 A1 | 5/2007 |
| WO | 2007/104045 A2 | 9/2007 |
| WO | 2008/055308 A1 | 5/2008 |

* cited by examiner

RESPIRATORY SYSTEM

FIELD OF THE INVENTION

The present invention relates to a respiratory system for enhancing respiratory care patient comfort and compliance. The respiratory apparatus of the present invention can be used for humans as well as for veterinary purposes.

DESCRIPTION OF RELATED ART

During respiratory care treatments a respiratory gas is delivered to the patient. However, as soon as the respiratory care treatment has started, potential side effects often arise which are not due to the original root cause for which the external respiratory assistance was needed in the first place.

As an example, but not limited to, serves the case of a patient which is diagnosed with Obstructive Sleep Apnoea (OSA). In OSA patients, the tongue and uvula partly or completely block air from moving down the throat to the lungs. During Continuous Positive Airway Pressure (CPAP) treatment an air flow is delivered to the patient, allowing air to pass down the throat of the patient to the lungs. Due to the high air flow rates, the airways are not able to deliver sufficient heat and moisture. The result is that the airways lose moisture and finally will show symptoms like drying of the upper airways and infections such as dry nose, dry throat, headache, painful chest, damage of weak tissue around nose entry, bleeding nose, dry and damaged lips, infections of nose, throat and sinus, . . . . In order to avoid these side effects the air flow is usually heated and humidified before being delivered to the patient.

As the heated and humidifier air travels along the conduit, some heat is lost to the air outside of the conduit resulting in condensation of the breathable gas. In order to avoid condensation within the hose of the conduit, the hose usually comprises a heating element provided for heating the breathable gas, counteracting the heat lost along the length of the hose. Conventional electrically heated hoses make use of a heating element in the form of a resistance wire. In order to provide the heating element with the right heating the hose usually comprises one or more sensors to measure the temperature of the breathable gas, this information being provided back to a controller which is associated with the heating element. This is for instance described in WO-A-2006019323. The use of additional separate sensors is not always desired. In order to overcome the use of additional sensors, US 2003059213 describes to use a heater element in the form of an electrical resistance heater exhibiting a positive temperature behaviour. The resistance of a positive temperature coefficient (PTC) material increases markedly once it reaches a threshold temperature. A problem with PTC materials is that upon overheating they melt down. So overheating of the resistance, which may occur, causes permanent damage and the whole conduit has to be replaced.

Literature references indicate that for CPAP therapy the optimal temperature and humidity of the air are 30° C. containing 95% relative humidity or about 30 mg water per liter of air absolute humidity. Literature references further indicate that for ventilation the optimal temperature and humidity of the air are 37° C. containing 100% relative humidity or about 44 mg water per liter of air (absolute humidity).

The mentioned ideal absolute humidity and temperature are important parameters that will determine the comfort of the ventilated patient, reduce the unwanted side effects of the therapy and hence contribute to the compliance of the patient. However, tests prove that neither of the tested humidifier systems, when operated under normal ambient conditions, i.e. normal ambient temperature, or challenged ambient conditions, i.e. low ambient temperature, are able to deliver the required optimal setting for temperature and humidity but stay well below this optimal setting. By increasing the temperature of the water reservoir of the humidification chamber of the humidifier system, a headspace is created that is warmer and more humid. However, the maximum temperature of the humidification chamber is restricted since, at too high temperatures, the air flow will contain a too high amount of moisture that, once passing through the outlet hose and being cooled down by ambient temperature, will start to condensate in the outlet hose, i.e. the hose connecting the humidifier system and the patient interface. Condensation is a very undesirable phenomenon in ventilation and CPAP therapy. Condensation happens when the ambient temperature cools the outlet air, i.e. the air leaving the humidifier system, down below its dewpoint temperature. This can happen when the ambient temperature is lower than the dewpoint temperature of the breathable gas. By condensation, water is removed from the airflow and as a result, the dewpoint will decrease. Equilibrium is reached when the outlet air flow is cooled down to its new dewpoint, which is ambient temperature.

To try and solve this issue, heated outlet conduits were developed to counteract the cooling effect of the ambient temperature and to maintain or increase temperature in the outlet air over the length of the outlet conduit. The ultimate goal is to have a temperature at the outlet of the hose that is still higher than the dewpoint despite the cooling effect of the ambient conditions. F&P HC 600 with Thermosmart® technology is considered the benchmark in humidifier systems. This machine was able to increase outlet temp and avoid condensation by significantly increasing the temperature of the outlet air. However, due to the heating relative humidity dropped and more importantly, the machine was not able to deliver the optimum absolute humidity of 30 mg water/liter air necessary to maximize patient comfort. This drills down to the basic property of a humidifier system that, in essence, was not able to deliver sufficient absolute humidity to the air flow coming into the reservoir due to the restricted maximum temperature. Due to the restricted maximum temperature, the water bath can transfer a limited amount of humidity depending on the heat capacity of the water at that maximum temperature. It is of utmost importance that this outlet air does not cool down to avoid condensation. In extreme conditions (cold ambient temperature), the inlet air has a lower capacity to hold water compared to high ambient temperature inlet air. As such, this cold air will extract energy from the heated humidifier, thereby reducing its efficiency to maximize humidity uptake in the humidifier and thereby reducing the dewpoint of the outlet air. A reduced dewpoint means less absolute humidity so less comfort for the patient. In case of a heated outlet hose, temperature can be increased but humidity will be suboptimal due to restrictions on the temperature of the humidifier and the limited capacity of the inlet air to hold moisture. In particular, the heated outlet hose does help to maintain or increase temperature of the air flow coming out of the humidifier chamber, thereby contributing to reducing the risk for condensation, but the heated hose does not contribute to increasing the absolute humidity of the airflow delivered to the patient. As a consequence, even the F&P benchmark 600 series with HH is not able to provide the 30 mg water/liter of air (as claimed in the product literature), especially in challenged conditions (cold ambient temperature).

Another problem arises when heated and humidified air leaving the humidification chamber is passed through an inspiratory hose versus a respiratory mask. The air breathed out by the patient is passed through an expiratory hose back to the humidification chamber. However, because of the high amount of moisture of the air and because of the temperature difference between the ambient temperature and the temperature of the air delivered to the patient and the air breathed out by the patient, the air is likely to start to condensate in the hoses and the respiratory mask.

Previous attempts to avoid the problem of condensation all involved heating the gases in the inspiratory hose or in the expiratory hose. The mask is however exposed to the highest concentration of moisture and greatest temperature differences and thus has the highest risk to the occurrence of condensation.

Another problem with current respiratory systems is that they are very costly. Because most parts of the respiratory system are integrated and fixedly attached to one another, practically the whole system needs to be replaced in case there is damage to one or more of the respiratory parts. This results in very high replacement costs for the patient. Moreover, the current respiratory systems offer few flexibility to the patient. Because most of the parts are fixedly attached to one another, it is difficult to upgrade the system once therapy has started. Another problem is that the patient is not able to adjust the settings, within clinical limits, such that the most comfortable conditions are achieved from a patient's perspective. The respiratory care parameters are pre-set by the doctor at the moment of the diagnosis. However, because ambient conditions may be different at home compared to clinical conditions, the same results are not always achieved at home. It is therefore desirable that a respiratory system is provided, which is on a long term cost efficient for the patient, easily up-gradable, which enables the patient and/or nursing staff to achieve the most comfortable conditions in a convenient way ensuring maximum compliance at the lowest possible cost of ownership. The comfortable conditions are may be chosen within two limits. The most desirable conditions for the specific respiratory therapy will not exceed the conditions known to cause damage, like temperatures higher than 41° C. Alternatively, similar damage causing conditions can be defined for other relevant respiratory related parameters, like pressure, air-flow etc. which should not be exceeded. From a lower limit, certain conditions can be defined causing discomfort, as an example, but not limiting, like humidity levels which cause the upper airways to dry causing bleeding noses, headaches etc. Alternatively, similar discomfort causing conditions can be defined for other relevant respiratory related parameters, like temperature, pressure, air-flow etc.

The following definitions are provided:
Absolute Humidity:
Definition: Absolute Humidity is the actual amount of water vapor in a liter of gas
One liter of gas at 37° C. contains 22 mg of water vapor. Its Absolute Humidity is therefore 22 mg/L.
If we add more water vapor to this gas, its Absolute Humidity will increase.
Clinical Example: By the time gases reach the lung, they have been warmed to 37° C. and contain 44 mg/L absolute humidity.
Relative Humidity
Definition: There is a limit to how much water vapor a gas can hold at a certain temperature. Relative Humidity measures how much water vapor a gas is holding compared to how much it can hold at that temperature.
One liter of gas and contains 22 mg of water vapor. At 37° C., this gas can hold 44 mg of water vapor, but it is only half full currently, with 22 mg. i.e. 50% Relative Humidity.
If another 22 mg of water vapor is added the gas will reach its maximum capacity to hold water vapor and the Relative Humidity is now 100%.
Clinical Example: The mucociliary transport system works at its maximum rate when inspired gases are conditioned to 37° C., 100% RH. This represents 44 mg water vapor per liter of gas.
Dewpoint
This is the temperature where a gas is 100% Relative Humidity (full of water vapor). If a gas cools below this temperature, water vapor is lost as condensation.
Clinical Example: the gas within a humidified breathing circuit is warmer and holds more vapor than the surrounding air. Unless the humidified gas is kept above its dewpoint by using for example a heated wire breathing circuit, the gas will cool and the water vapor will be lost as condensation.

SUMMARY OF THE INVENTION

It is a first aim of the invention to provide a heating element which allows repeatable detection and reduction of overheating inside of the conduit.

This first aim is achieved with a conduit showing the technical characteristics of the first independent claim.

It is a second aim of the invention to provide a process for manufacturing a conduit in which at least one wire can be inserted in a simplified way.

This second aim is achieved with a manufacturing method showing the technical steps of the second independent claim.

It is a third aim of the invention to provide a conduit in which at least one wire may be incorporated in a cost-efficient way.

This third aim is achieve with a conduit showing the technical characteristics of the third independent claim.

It is a fourth aim of the invention to provide a respiratory system which comprises humidifier system which is able to approximate more closely the optimal settings of temperature and humidity.

This fourth aim is achieved with a humidifier system showing the technical characteristics of the fourth and/or fifth independent claim.

It is a fifth aim of the invention to provide a re-usable cuff which allows measurements of respiratory care parameters on whatever location within the respiratory system.

This fifth aim is achieved with a cuff showing the technical characteristics of the sixth independent claim.

It is a sixth aim of the invention to provide a respiratory mask in which the occurrence of condensation of the breathable gas inside the mask is avoided.

This sixth aim is achieved with a mask showing the technical characteristics of the seventh independent claim.

It is a seventh aim of the invention to provide a cost-efficient, upgradeable respiratory system.

This seventh aim is achieved with a modular respiratory system showing the technical characteristics of the eighth independent claim.

Two or more of the mentioned aspects of the invention may be combined or may be part of a further aspect of the invention. It is for instance possible to incorporate the conduit according to a third aspect of the invention into a modular respiratory system according to an eighth aspect of the invention, to incorporate a respiratory mask according to a seventh aspect of the invention into a modular respiratory system according to an eighth aspect of the invention, and so on.

In a first aspect of the invention, a conduit for use in a respiratory system is proposed which comprises a hose, connectable between two parts of a respiratory system, and a heating element, provided for heating the breathable gas under control of a controller, wherein the heating element comprises a negative temperature coefficient ("NTC") component.

The resistance of a NTC material decreases once it reaches a threshold temperature. Preferably, the NTC component is composed to provide a threshold temperature at or just above the preferred gases temperature. As a result, the heating elements, comprising such a NTC component, can be used themselves as a control element and eliminate the need for additional sensors or thermocouples to measure and control the temperature of the breathable gas. In fact, when the preferred gases temperature is reached, the resistance of the NTC component will decrease. This information may then be transferred to a controller which will decrease the power supply to the heating element and as such, reduce the temperature of the breathable gas.

Furthermore, the presence of the NTC component also allows the heating element to detect and minimize locally overheating inside the conduit in a repeatable manner. When overheating occurs near the NTC component, for instance as a result of a hot spot of the heating element, the resistance of the NTC component will decrease rapidly in view of the logarithmic relationship between the resistance of an NTC material and the temperature. This information can be provided to a controller which can more rapidly decrease the power supply to the heater element with respect to the prior art, thereby avoiding permanent damage to the conduit. Furthermore, analysis has shown that NTC components are less prone to be permanently damaged than PTC materials. As a result, the NTC component enables a repeatable detection and reduction of overheating inside the conduit. Summarizing, the conduit according to the first aspect of the invention comprises a heating element which provides for heating and controlling of the temperature within the hose of the conduit and for repeatably detecting and reducing the occurrence of overheating spots on specific locations within the hose.

The heating element with the NTC component may take any form considered suitable by the person skilled in the art. Preferably, one or more NTC components is/are provided over substantially the entire length of the hose, such as for example a series of NTC thermistors along the hose. This configuration allows detecting and minimizing overheating over substantially the entire length of the hose. From the moment there is, somewhere along the hose, a section which is locally overheated, the resistance of the NTC component at this section will decrease rapidly. This information can then be provided back to a controller which can decrease the power supply accordingly.

Preferably, the heating element takes the form of a heating cable in which an NTC component is incorporated. This type of configuration is in particular suitable to detect and minimize hot spots in the heating wire. Hot spots are short sections in the heating wire which show a much lower resistance compared to the surrounding sections. In the prior art, such a hot spot could result in melting through of the hose wall. In this preferred embodiment, if there is a hot spot somewhere along the heating cable, the resistance of the NTC component will decrease enabling reduction of the power supply before melting of the hose wall at the hot spot occurs. This can further ensure the repeatability of the overheating detection in the first aspect of the invention.

Preferably, the heating element forms a co-axial cable construction which extends in longitudinal direction of the hose, the cable construction comprising two electrical wires, one of which being a heating wire and the other being provided for feedback purposes, the two electrical wires being separated by the negative temperature coefficient component. Such a co-axial cable construction has the advantage that it has a very small diameter, so that it can be associated with the hose in a number of different ways, such as for instance in a rib in the wall of the hose, in a wire groove at the inside of the hose or the outside of the hose, wound like a spring, . . . .

In a second aspect of the invention a method for manufacturing a conduit is proposed in which a heater wire can be inserted in a wall of the hose in a simplified, fast and cost-efficient way. The method comprises a first step in which a blowmoulded tube is formed comprising at least one helical wire groove on the exterior or interior surface of the tube and a second step in which at least one wire is inserted in one or more of the at least one wire groove. The forming blocks of the corrugator are shaped in such a way that the at least one helical wire groove is formed upon blowmoulding the tube. The wire can be a heating wire, a communication wire, a combined heater and communication cable or any other wire or cable.

Blowmoulded tubes or hoses may have a so-called corrugated wall of protrusions alternating with recesses. These corrugations may progress helically in longitudinal direction of the tube or hose. Advantageously, the helical wire groove(s) can be formed by the recesses in between such helical corrugations of such a corrugated blowmoulded tube.

Alternatively, the tube may comprises a helical wire groove with a different pitch with respect to that of the hose corrugations (which do not necessarily have to be helical). The pitch of the hose corrugations in general serves a different purpose than that of the wire groove. In general, the pitch of the hose corrugations is related to the strength and flexibility of the hose, whereas the pitch of the wire groove is for instance related to the amount of energy/heat which has to be transferred to the fluid which is passed through the hose. The pitch of the wire groove(s) determines the length of the wire that is inserted into it. The higher the length of the wire is, the higher the cost of the overall system. So it may be advantageous that the hose corrugations and the wire groove(s) have a different pitch. In case the pitch of the wire groove differs from that of the hose groove, it is for instance possible to have a hose with high strength, i.e. wherein the corrugated wall of the hose has a zero or small pitch, combined with a cost-efficient hose in which not too much wire is consumed, i.e. wherein the wire groove has a higher pitch.

The method according to the second aspect of the invention can therefore provide in a cheaper conduit and in a reduction of the overall weight of the conduit. Another advantage is that the method according to the second aspect of the invention allows manufacturing a hose in which at least one wire can be inserted, with a simplified and automated process.

The pitch of the wire groove can be constant or can vary in longitudinal direction of the hose. The latter is for instance done in case a heater wire is inserted and an intensive heating is for instance desired in the centre of the hose and a less intensive heating is desired near the edges of the hose.

It is further possible to vary other properties of the helical wire groove, such as the width and height of the wire groove. The variation of these properties can for instance be used to influence the accessibility of the at least one wire. By varying the width of the helical wire groove for instance, the at least one wire may be more or less positioned in the groove. Preferably, the shape of the wire groove (in cross-section) is such that the at least one wire is clamped within the wire groove. Varying the diameter of the helical wire groove may for instance be desired in case use is made of hoses with varying diameter, for instance for use in hoses for CPAP systems where the diameter of the hose changes versus the patient interface.

The at least one helical wire groove can be wound clockwise or counter clockwise. One helical wire groove can be used to carry multiple wires, whereas different wires can have different purposes. One wire can for instance be used for heating the fluid passing inside the hose in order to avoid condensation inside the tube. Another wire can be used for carrying signals for communication and power for the patient mask of the CPAP unit.

Preferably, the method according to the second aspect of the invention is characterized in that in the first step multiple helical wire grooves are formed on the exterior or interior surface of the tube. Each of the wire grooves can be provided for carrying one or more wires. Some of the wire grooves may not carry any wires. Different wire grooves can have the same or a different pitch. In this way different wire grooves can for instance be used to carry wires which serve different purposes. A helical wire groove for carrying heater wires will usually have a smaller pitch than a helical wire groove for carrying communication wires. Different wire grooves can also differ in width and height, depending of the type and number of wires to be carried. Different wire grooves can both be wound clockwise or counter clockwise or one can be wound clockwise and the other counter clockwise. By varying the relative position of the different wire grooves, it is possible to provide the hose with more and less accessible wires. Preferably, the different wire grooves extend parallelly, i.e. in a dual, triple or multi-pitch configuration.

The method for manufacturing a conduit according to the second aspect of the invention preferably comprises an additional step in which an additional layer is extruded at the inside of the tube for forming a smooth bore. A multilayer smooth bore hose formed with the method according to the second aspect of the invention has the advantage that a breathable gas passing through the hose encounters less resistance compared to a tube with a corrugated inner surface.

Preferably, the method according to the second aspect of the invention further comprises an additional step in which an additional layer is extruded at the outside of the tube for closing the at least one wire groove and as such, encapsulate the at least one wire which was inserted into the at least one wire groove. This additional layer can cover the entire hose or can be applied to only cover the wires.

In a third aspect of the invention a conduit for use in a respiratory system for supplying a breathable gas from a flow generator to a patient interface is proposed, the conduit comprising a hose connectable between two parts of the respiratory system, the hose being a multipitch hose comprising at least two parallelly extending helical ribs and at least one of the ribs holding at least one wire.

The conduit according to the third aspect of the invention provides in an alternative simplified way of incorporating at least one wire in the hose of a conduit. In fact these ribs can be created directly from the extrusion machines, whereas the parallel extending helical ribs have a different starting position on the extruder. An alternative could be to make the conduit web as a linear profile strip. In this form the wire if being used would again be located within the profile. Then one or more profile strips are wound in a helical form, as a second process, to produce the conduit. This technique of manufacturing a flexible hose by helically winding a web is known per se in the field of hose manufacturing and therefore needs no further explanation here.

The conduit according to the third aspect of the invention further has the advantage that the production speed of the conduit can be increased and thus manufacturing costs may be reduced. Another advantage is that the conduit may have a lower consumption of expensive wire materials, since the pitch of the ribs can be chosen.

The conduit according to the third aspect of the invention further has the advantage that a large number of wires can be integrated into the hose of the conduit in a fast and cost-efficient way. This can be understood from the fact that more than two helical ribs can be provided. By increasing the number of ribs, the number of wires may be increased accordingly by a factor relating to the number of pitches. Moreover, it is possible to include more than one wire into one rib. As such, the conduit according to the third aspect of the invention is in particular suitable for holding at least 4 wires.

The at least one wire may be a heater wire, a communication wire, or a combined cable construction as shown in FIGS. 1 and 2 or any other wire or cable. Only one of the two (or more) helical ribs may contain a wire, or both of the helical ribs may contain a wire. One helical rib can be used to carry multiple wires, whereas different wires can have different purposes. One wire can for instance be used for heating the passing fluid inside the hose in order to avoid condensation inside the tube. Another wire can be used for carrying signals for communication and power for the patient mask of the CPAP unit. The two helical ribs may serve different functions. The first helical rib may carry heater wires, whereas the second helical rib may carry communication wires. As a result, the conduit according to the third aspect of the invention may offer a greater number of functions if required, due to the availability of more signal capacity.

The at least one wire may comprise a co-axial cable construction which comprises a PTC or NTC component, provided for detecting and reducing the occurrence of overheating within the hose.

The pitch of the helical ribs can be constant or can vary in longitudinal direction of the hose. The latter is for instance done in case a heater wire is inserted and an intensive heating is for instance desired in the centre of the hose and a less intensive heating is desired near the edges of the hose. Each of the helical ribs can be provided for carrying one or more wires. Some of the ribs may not carry any wires. Different ribs can also differ in width and height, depending of the type and number of wires to be carried. The conduit may comprise more than two helical ribs.

The conduit according to the third aspect of the invention may have a smooth inner layer, such that the breathable gas passing through the tube encounters less resistance compared to the tube with a corrugated inner surface.

In a fourth aspect of the invention a respiratory system is proposed which comprises a humidifier system, the humidifier system comprising an inlet for taking in a breathable gas and a humidification chamber connected to the inlet for heating and humidifying the breathable gas before delivery to a patient. The respiratory system according to the fourth aspect of the invention further comprises a pre-conditioning system for pre-conditioning the breathable gas at the inlet before entry into the humidification chamber in a controlled manner.

By preconditioning the breathable gas at the inlet before entry into the humidification chamber in a controlled manner, the performance of the respiratory system can be improved. In fact, by pre-conditioning the breathable gas, the respiratory system will be able to approximate more closely the optimal settings for temperature and humidity. Because the ideal absolute humidity and temperature are important parameters that can determine the comfort of the ventilated patient and that can avoid unwanted side effects as a result of the treatment, the respiratory system according to the fourth aspect of the invention can also improve patient comfort.

Because the pre-conditioning is done in a controlled manner these optimal settings can be approximated independently from the ambient conditions in which the respiratory system is operating, i.e. in normal conditions, i.e. normal ambient temperatures, as well as abnormal conditions, i.e. cold ambient temperatures. Another advantage of pre-conditioning the breathable gas is that the risk for condensation in the respiratory system may be further reduced independently from the ambient conditions in which the respiratory system is operating. This is because the design of the humidification chamber can be better optimized for reaching optimum humidity and temperature levels in the breathable gas, since variations in the temperature and humidity levels at the inlet can be largely cancelled out by the controlled pre-conditioning.

In a preferred embodiment of the respiratory system according to the fourth aspect of the invention, the pre-conditioning system comprises a temperature control system for influencing the temperature of the breathable gas at the inlet before entry into the humidification chamber.

The temperature control system preferably comprises an inlet heating element, provided for heating the breathable gas before entry into the humidification chamber, and a controller, provided for controlling the inlet heating element. The pre-heated breathable gas can be generated with any heating element considered suitable by the person skilled in the art. The pre-heated breathable gas can for instance be generated with a heating element internal in the inlet hose of the humidifier system, a heating element external to the inlet hose of the humidifier system, with a heating element incorporated in the flow generator, . . . . The controller may be any type of controller considered suitable by the person skilled in the art, such as for example a controller which is incorporated into the conduit of the respiratory system or an independent controller. By pre-heating the inlet air, i.e. the air entering the humidification chamber, in a controlled manner, the temperature of the inlet air can be increased from ambient to a certain setpoint, which can be maintained irrespective of changes in ambient conditions.

An advantage of such a respiratory system is that it has a higher capacity to hold humidity and is able to take up more humidity from the humidifier. Another advantage of the respiratory system according to the fourth aspect of the invention is that the pre-heated breathable gas has a higher heat capacity, which results in a reduction of the energy extraction from the humidifier and an optimization of the efficiency of the humidifier.

In another preferred embodiment of the respiratory system according to the fourth aspect of the invention, the pre-conditioning system comprises a humidity control system for influencing the humidity of the breathable gas at the inlet before entry into the humidification chamber.

By pre-humidifying the inlet air, the humidity of the inlet air is increased from ambient to a certain setpoint. The humidification can be generated with any humidification element considered suitable by the person skilled in the art. The humidification can for instance be done by a second humidifier system integrated in the flow generator. An advantage of such a respiratory system is that the pre-humidified inlet air has a higher humidity level, which results in a reduction of the energy extraction from the humidifier and an optimization of the efficiency of the humidifier.

The pre-conditioned breathable gas may be both pre-heated and pre-humidified.

The pre-conditioning system may comprise any sensor considered suitable by the person skilled in the art to control the temperature and/or humidity of the breathable inlet gas. The pre-conditioning system may comprise one or more of these sensors.

The controller may for instance use the ambient air temperature and/or the ambient air humidity, measured by at least one sensor provided in the pre-conditioning system, to set the inlet air temperature and/or to set the inlet air humidity. In this way, the performance of the respiratory system is less dependant of the ambient conditions and the optimal settings can be approximated independently from the ambient conditions in which the respiratory system is operating.

Instead of the ambient air sensors, or in addition thereto, the controller may use a dewpoint system for determining the dewpoint temperature of the breathable gas. The dewpoint system may be any means considered suitable by the person skilled in the art. The dewpoint system for example comprises two sensors, one for measuring the temperature of the breathable gas, and one for measuring the humidity level of the breathable gas, but the dewpoint system may for instance also be a combined dewpoint sensor. The dewpoint system may be placed on whatever location in the respiratory system, preferably close to the inlet of the humidification chamber of the humidifier system. By determining the dewpoint temperature of the breathable gas, the temperature and humidity of the breathable gas can be controlled in such a way that its temperature stays well above its dewpoint temperature and well above the ambient dewpoint temperature, such that condensation of the breathable gas can be avoided.

In a fifth aspect of the invention a respiratory system is provided, which comprises a humidifier system in which the temperature of the outlet gas, i.e. the breathable gas leaving the humidification chamber of the humidifier system, is controlled.

The respiratory system according to a fifth aspect of the invention comprises a humidifier system which comprises an inlet for taking in a breathable gas and a humidification chamber connected to the inlet for heating and humidifying the breathable gas. A conduit connects the humidifier system to the patient interface. The humidifier system further comprises a heating system, associated with the conduit and provided for heating the breathable gas delivered from the humidifier system to the patient interface. The heating system comprises a heating element and a dewpoint system for determining the dewpoint of the breathable gas. Both the dewpoint system and the heating element are in communication with a controller of the respiratory system.

This respiratory system allows controlling the temperature of the gas leaving the humidification chamber based on the dewpoint temperature of the breathable gas. The dewpoint temperature is provided back to a controller, which is in communication with a heating element of the humidifier system. This system can be used to set the temperature of the air leaving the humidification chamber higher than the dewpoint temperature of the breathable gas to avoid condensation of the breathable gas inside the conduit.

The dewpoint system for determining the dewpoint temperature of the breathable gas can be provided for determining the dewpoint on any location of the respiratory system considered suitable by the person skilled in the art. The dewpoint system can for instance by determined close to the humidification chamber or at a position near the patient interface. Optionally, the respiratory system may comprise multiple locations where the dewpoint is determined. By determining the dewpoint at a first location near the humidification chamber and a second location near the patient interface, condensation inside the conduit can be further reduced.

The dewpoint system can be any system considered suitable by the person skilled in the art which allows determining the dewpoint. The dewpoint system can for instance comprise a separate temperature and humidity sensor combined with a processor which, based on predetermined tables, determines the dewpoint based on the temperature and humidity measurements of the separate sensors. The dewpoints sensor can for instance comprise an integrated dewpoint sensor which directly determines the dewpoint and provides it back to a controller.

Optionally, the humidifier system of the respiratory system according to the fifth aspect of the invention may comprise additional sensors, for instance pressure sensors, which allow further control of the gas leaving the humidification chamber.

The dewpoint temperature of the breathable gas can additionally be used to control any other heating elements of the respiratory system considered suitable by the person skilled in the art, such as a heating element connected to the hose connecting the humidifier system and the patient interface. This allows further reducing the risk to condensation within the conduit.

In a sixth aspect of the invention a cuff is proposed which is removably connectable between two parts of a respiratory system. The cuff according to a sixth aspect of the invention comprises a passage for a breathable gas flowing in the respiratory system and comprises at least one integrated sensor for measuring respiratory care parameters of the breathable gas.

Because the cuff is removably connectable between two parts of a respiratory system, it does not need to be thrown away together with that part of the respiratory system that needs to be replaced. For instance, in case the hose needs to be replaced, the cuff which is connected to the hose can be re-used to connect to a replacement hose. This results in reduced replacement costs.

Another advantage of the cuff according to a sixth aspect of the invention is that, if a patient requires an upgrade of its respiratory system, it does not necessarily need to replace its complete conduit system. It may be sufficient to replace the cuff with another cuff that comprises more or other sensors or more or other integrated communications tools.

The cuff is in particular suited for use in a modular respiratory system where two or more parts are removably connectable to each other. Using modular technology means that the patient can have more flexibility and patient enhancement at a longer term reduced cost. If required the technology can be enhanced and more reliable components can be used as the cuff cost will be distributed over a number of users, and not just as a single use consumable. The modular design will assist in manufacturing and distribution. The different parts of the respiratory system can be made on different location, even in different countries. Another advantage is that the cuff allows the user to select the best fit for their situation. Another advantage of the cuff according to a sixth aspect of the invention is that the cuff can be tailor made for one specific application or treatment, without needing to replace the hose itself. Another advantage is that the complex electronics for measuring and controlling the respiratory care characteristics do not need to be installed into the hose, but may be incorporated into the cuff, which results in a reduction of long term costs for the user.

The cuff is designed in such a way that it can connect to any part of the respiratory system, for instance a human machine interface with a hose, two interconnecting hose sections, a controller to a hose, . . . . The cuff can be positioned on any location within the respiratory system. The cuff can for instance be located directly onto the humidifier system or flow generator and be used to measure parameters as temperature, airflow, and humidity of the breathable gas. The cuff can be connected to the patient mask. This means that the cuff can contain some mask technology such as venting and pressure measurement, O2 concentrations, CO2 concentration, air flow rate, . . . . This allows a direct measurement and control of all relevant measurement respiratory care parameters of the breathable gas. In current respiratory systems, the control is indirect and potentially complex, delayed, expensive and subject to high level of signal noise. This is due to the fact that, in current respiratory systems, the control of the system is usually done by the unit. Usually, the unit, i.e. ventilator unit, positive air pressure device, anesthesia unit, contains the measurement instruments and electronics to control the relevant parameters, for instance air flow, pressure, anesthetic gas concentration, oxygen concentration, to monitor the patient's condition. However, when the air flow exits the conduit, there is no direct measurement of the air flow whereas the airflow might have decreased due to the resistance level of the hose. This is similar for pressure. Pressure is generated by the unit. However, no pressure is measured near the patient. Pressure drop will occur over the hose but is not measured directly. Due to the absence of measuring devices near the patent interface, the units rely on indirect measurements, for instance ambient temperature measurements, that are not localized near the patient interface and as such, software needs to include all kinds of compensation algorithms to control or adjust the output of the unit. In some therapies, the expired air is conducted back to the unit to perform measurements. However, due to the absence of measuring devices near the patient interface, the units rely on indirect and delayed measurements and as such, software needs to include all kinds of compensation algorithms to control or adjust the functioning of the unit. Because the cuff can be connected directly onto the patient interface, signals are generated at the right location and may be transferred directly to the unit allowing accurate monitoring and control.

Preferably, the at least one sensor is located in the passage of the cuff, such that it can directly measure any characteristics of the breathable gas passing through. The at least one sensor of the cuff can also be located somewhere else, for instance in the wall of the cuff.

Preferably, the cuff is designed in such a way that it may click on any part of the respiratory system. The click-on system preferably works in conjunction with a compatible cuff on that part of the respiratory system where it is attached to and which incorporates single or multiple wire systems either integrated in the hose construction or loosely or fixed inserted flat in the conduit or attached to the outside of the hose. The communication between the click-on cuff can also be done independent of the hose by either loose connection wires or wireless transmission. The benefit of this system is that the click-on cuff provides the functionality needed to generate the signal at the patient interface whereas the communication conduit carries the signal to the independent control unit or ventilation unit. The click-on cuff is designed for long time repeated use whereas the communication conduit can be designed as a disposable product or as a reusable product.

In a seventh aspect of the invention a respiratory mask is proposed which comprises a condensation reduction system for reducing condensation inside the mask. The respiratory mask can be any type of respiratory mask, nose masks as well as face masks. The mask can be made from hard or soft materials or a combination thereof. The condensation reduction system can be an active system, for example with an active heating element with which the breathable gas in the mask can be heated to avoid condensation, or a passive system, for example comprising insulation material to passively avoid cooling down of the breathable gas is the mask, or a combination of an active and a passive system.

According to a first embodiment of the respiratory mask according to the seventh aspect of the invention, said condensation reduction system comprises a heating element provided for heating the breathable gas. By sufficiently heating the breathable gas inside the gas, condensation of the gas within the mask can be reduced.

The element system can be located on any position of the mask. The heating element may for instance be attached to the outside and/or the inside of the mask, or may be embedded in the wall of the mask.

The heating element can be permanently integrated into the mask or can be made detachable from the mask. A detachable heating element has the advantage that it is re-usable, which results in lower replacement costs for the patient. Preferably the heating element comprises a heating part, preferably a heating mesh, attached to the outside of the mask and/or to the inside of the mask. The heating element may comprise an NTC (negative temperature coefficient) or PTC (positive temperature coefficient) material. Because the resistance of NTC and PTC materials changes with changing temperature, these materials can be used in itself as temperature sensors, controlling the temperature of the air. Alternatively, the heating element may comprise independent temperature sensors. The heating element can be constructed from standard heating wire. The heating element can also retrieve heat directly from the patient, so that a separate heat source can be avoided.

Preferably, the heating element is controlled by a controller of the respiratory system. The control is for instance based on dewpoint measurements of the breathable gas, preferably at a position near the patient's mask. By heating the breathable gas to a temperature above its dewpoint temperature, condensation inside the mask may be reduced. The control of the heating element may be based on any other respiratory care parameters considered suitable by the person skilled in the art. The use of a control has the advantage that the performance of the mask can be made less dependant on the ambient conditions.

The heating element can be controlled via an independent controller or any system integrated controller. The controller can connect to said mask via direct leads or terminal connections. The controller can be connected to the mask via a cuff according to a sixth aspect of the invention. The controller can utilize electrical swivel connections either at the mask connection and/or at the feed connection. These connection leads can be integrated into the hose construction or can be independent flying leads. The heating element may for instance be controlled via a hose with integrated control wires. The leads can be integrated into the inspiratory or expiratory hose.

In order to avoid contact between the heating system and the respirated air, the heating element is preferably isolated from the air. This may for instance be achieved by providing the heating element inside a cavity inside the mask. The presence of a sealed cavity inside the mask allows sterilization of the respiratory mask. The heating element can have a variety of shapes adjusted to the different shapes of the mask.

According to a second preferred embodiment of the respiratory mask according to the seventh aspect of the invention, said system comprises a thermally insulating system for thermally insulating at least part of said mask from ambient conditions.

The insulating system provides for an improved insulation of the moisturized inspiratory and expiratory air from the ambient temperature, which results in a reduced occurrence of condensation within the patients mask.

The insulating system may be any kind of insulating system considered suitable by the person skilled in the art. The respiratory mask may for instance comprise a thermally insulating material which covers at least part of the respiratory mask.

Preferably, the respiratory mask has a double wall formed by an outer layer and an inner layer, which provides for improved isolation. Preferably, the inner and outer layers enclose a sealed cavity. In order to reduce the thermal conductivity from outside the mask to the inside of the mask, the sealed cavity preferably comprises a vacuum or is filled with air or any other thermal insulating material or material with low level of thermal conductivity known to the person skilled in the art.

The respiratory mask may comprise both a heating system as an insulating material. This type of mask provides in a further reduction of condensation of breathable gas inside the mask.

In an eighth aspect of the invention a modular respiratory system is proposed which comprises at least a flow generator, for pressurizing a breathable gas, a gas conducting system, for supplying the breathable gas from the flow generator to a patient interface, and the patient interface for supplying the breathable gas received from the gas conducting system to a patient. The respiratory system is a modular system in which the gas conducting system is formed by removably connecting multiple gas conducting parts to each other.

Such a modular respiratory system results in a longer term reduced cost for the patient. If one of the respiratory system parts is damaged, it is not necessary to throw away the entire respiratory system, but it is sufficient to replace only that part of the system that is damaged. This results in lower replacement costs for the patient. Another advantage is that the patient can first buy a more "standard" respiratory system and later on upgrade his standard respiratory system as he wants. The patient can for instance add a humidifier system, a controller, a human machine interface or any other part to the standard respiratory system. Another advantage is that the modular design allows manufacturing different parts on different locations and/or in different countries and/or by different companies.

The gas conducting system of the respiratory system according to the eighth aspect of the invention may comprise a conduit of one single length. Alternatively, the conduit may be formed by a number of shorter length interconnecting conduit sections which are removably connectable to each other.

These interconnecting conduit sections have the advantage that it is possible to extend the existing conduit if required. Using for instance interconnecting conduits of 0.6 m single length, the user can for example make a piece of conduit of 1.8 m from 3 pieces of interconnecting conduit sections.

Another advantage of these interconnecting conduit sections is that not the whole conduit has to be replaced in case of damage to the conduit. It is sufficient to replace only the individual damaged interconnecting conduit. These interconnecting conduits allow thus to reduce replacement costs.

Preferably, the respiratory system according to the eighth aspect of the invention further comprises a humidifier system for heating and humidifying the breathable gas to be supplied to the patient which is removably connectable between two parts of the gas conducting system. The connection of the humidifier system to the parts of the gas conducting system can be done in any way considered suitable by the person skilled in the art. The humidifier system may for instance directly connect to a conduit section or via a cuff according to the sixth aspect of the invention or any other connection system. The humidifier system may be any type of humidifier system, but preferably is a humidifier system according to the fourth and/or fifth aspect of the invention. Preferably, in order to further increase the performance of the humidifier system, at least part of the humidifier system is thermally insulated from ambient conditions. As a result, the performance of the humidifier system can be made less dependant on the ambient conditions and is able to perform better in challenged conditions. As such, even at restricted power consumption, the humidifier is able to generate more humidity compared to a humidifier without insulation.

Preferably, the respiratory system according to the eighth aspect of the invention further comprises a cuff according to the sixth aspect of the invention. The cuff can be used to removably connect any parts of the respiratory system, such as for instance the conduit to the mask, two interconnecting conduit sections, the humidifier system to the conduit, . . . .

Preferably, the respiratory system according to the eighth aspect of the invention further comprises a controller section for controlling at least one respiratory care parameter of the respiratory system.

The controller can be used to control any respiratory care parameter. The controller can for instance provided for controlling the heating of a hose and/or a humidifier to provide the patient with the correct breathable gas temperature and/or with the correct humidification levels. The controller can for instance be used to control the temperature, humidity, gas/fluid concentrations, gas/fluid flow rates and pressure of the medium which is passed through the hose. The controller can also be used to control other items of the hose systems, for instance the temperature and humidity level inside the patient's mask. Preferably, the set up of the controller is such that condensation inside the hose system, i.e. inside the hose and/or the mask, is avoided. The controller can be used to control one hose system or multiple hose systems.

The controller can be used for controlling additional systems, for example humidifiers, CPAP units and ventilation systems. The controller can be used for controlling additional heating systems, such as therapeutic blankets, heated joint pads or bed blankets.

The controller may be any type of controller considered suitable by the person skilled in the art. The controller may be a controller which is integrated in the flow generator, a controller which is integrated into a controller section forming part of the gas conducting system or an independent controller, which is physically not connected to the respiratory system.

A preferred embodiment of the controller is a controller which is integrated into a controller section forming part of the gas conducting system. An advantage of such a system is that no communication link to another controller needs to be established, which may result in a reduction of the number of wires of the overall respiratory system. Preferably, the controller section comprises a passage for the breathable gas flowing in the respiratory system and at least one integrated sensor in the passage for measuring respiratory care parameters of the breathable gas. This results in a reduction of the amount of wiring needed to connect the sensors with the controller, compared to the existing systems where the sensors are usually provided external to the controller. Another advantage is that such a controller is not limited to the number of parameters that can be measured. In existing systems the number of parameters that can be measured is usually limited because each of the sensors need to be connected with the controller and the amount of wiring is limited. Such a controller further has the advantage that, if a patient requires an upgrade of its respiratory system, it does not necessarily need to replace its complete conduit system. It may be sufficient to replace the controller with another controller that comprises more or other sensors.

Such a controller is in particular suited for use in a modular respiratory system where two or more parts are removably connectable to each other, offering the same advantages as the removable cuff according to a sixth aspect of the invention.

Preferably, the respiratory system according to the eighth aspect of the invention further comprises a human machine interface (HMI) controlling respiratory care parameters of the respiratory system.

Preferably, the HMI is removably connectable to a part of the respiratory system. A removable HMI has the advantage that it is re-usable, cost-efficient and that it can be manufactured independent of the other respiratory parts. The human machine interface can also be fixedly connected to a part of the respiratory system or made physically independent of the respiratory system. An independent HMI has the advantage that it can be placed close to the patient or remote from the patient, such that it may be operated by another person.

Preferably, at least part of the respiratory system according to the eighth aspect of the invention comprises a thermochromic material. Thermochromic (TC) products change color in response to temperature fluctuations using TC substances like liquid crystals and leuco dyes. Today, liquid crystals are used in many products, including aquarium thermometers, stress testers, forehead thermometers, and other applications. While liquid crystal TC materials are extremely capable materials, they are very difficult to work with and require highly specialized manufacturing techniques. The other type of TC material is called a leuco dye and is commonly used in security printing, novelty applications such as temperature sensitive plastics and mugs, product labels, advertising specialties, and textiles.

The use of thermochromic materials in at least part of the respiratory system allow to visual indicate temperature and temperature change. It allows patients and nurses to monitor the temperature and observe temperature change without the need for exact readings from displays. The thermochromic material can act as a safety mechanism in components that are heated or become warm upon use, for instance in a hose which comprises a heating element for heating a breathable gas. As soon as a threshold temperature is exceeded, the patient or nurse will be triggered by the color change.

In general, thermochromic materials can be applied in a respiratory system to act as a communication to visualize messages on heated respiratory parts, such as warning messages, company brand names, logos or other visual identifications, . . . .

The thermochromic substances can be applied in a number of different ways.

As a first example, a respiratory part may be extruded using a thermochromic material which extends throughout the entire respiratory part using active TC substances or formulated active TC substances in the form of a masterbatch. Examples of extruded respiratory parts are a conduit or part of a respiratory conduit such as a rib of a hose or heated hose; a jacket material of cables or insulation material of wires such as heating wires and signal wires. The TC can be incorporated over the entire extruded part or in a section of the extruded part. As a second example, a respiratory part may be co-extruded using active TC substances or formulated active TC substances in the form of a masterbatch. Examples of co-extruded respiratory part are a respiratory conduit or part of a conduit such as a rib of a hose or heated hose, a jacket material of cables or insulation material of wires such as heating wires and signal wires. The TC material can be incorporated over the entire co-extruded part or in a section of the co-extruded part. As a third example, use can be made of injection moulding, low pressure injection or over-moulding using active TC substances or formulated active TC substances in the form of a masterbatch. Examples of injection moulded products are cuffs of hoses, in connectors, in humidifier parts such as humidifier chambers, in filters, Y pieces, . . . . The TC material can be moulded in the entire part or only in a section of the moulded part. As a fourth example, use can be made of in-mould labelling of a component treated with a TC substance to allow cost effective application of the TC substance. As a fifth example all kinds of surface treatments are possible, such as for example:
  a) Printing: TC substances can be printed directly on the substrate e.g. to visualize the brand name of a company, a temperature scale, logo etc.
  b) Painting: TC substance can be applied by liquid painting of a lacquer or water based solution or dispersion
  c) Spraying: TC substance can be applied by spraying powder or liquid
  d) Dipping: TC substances can be applied by dipping the substrate into a solution or dispersion of the active TC substance or any formulation thereof.
  d) Gluing
  e) Laser marking As a sixth example thermochromic components may be inserted into a part of the respiratory system. A thermochromic thermometer may for instance be inserted in the hose, cuff or respiratory mask of the respiratory system.

Preferably, at least part of the respiratory system according to the eighth aspect of the invention comprises an antimicrobial (AM) material.

The use of antimicrobial materials in the respiratory system has a number of advantages. AM materials provide additional hurdle in the prevention of ventilator associated pneumonia, an effect that often occurs with ventilated patients especially in hospitals and intensive care units. AM materials also provides additional hurdle in the prevention of cross-contamination, i.e. the patient becoming colonized and infected by external flora or internal flora. The incorporation of antimicrobial substances or the surface treatment with antimicrobial substances can help reduce the microbial counts in the respiratory system. AM property also provides protection against material degradation and odour formation.

The AM material can be applied to the entire respiratory system or only to certain part of the respiratory system. Preferably, the AM material is at least applied to those respiratory parts that are prone to develop microbial colonization (e.g. presence or availability of water/moisture/humidity, increased temperature, etc). AM treated respiratory parts can include, but are not limited to, the patient interface such as the respiratory mask (face mask, nose mask, tension straps, pressure cushion, etc) or the endotracheal tube, Y-pieces, the cuffs (sensing cuffs, communication cuffs, adaptor cuffs, connection cuffs, . . . ), the sensors or the coating on the sensors, the hose, the heated hose, the heating and signal wires inside the hose lumen or outside the hose, the humidifier system (e.g. humidifier chamber), the HMI, the controller, . . . .

AM materials may include organic (e.g. triclosan, zinc pyrithione, etc) and/or inorganic substances (silver-based substances, copper-based substances and combinations thereof, etc) and/or combinations thereof. AM substances can be migrating and non-migrating compounds providing AM activity e.g. by interacting with the cell membrane and/or by interaction with the cell metabolism or by destructing the cellular protection mechanisms (cell wall, cell membrane, etc). AM compounds can provide slow release of the active substance (e.g. silver based substances, encapsulated AM substances in matrices like zeolite or glass, etc).

In general, it is advised to apply AM substances in the top layer of an article in order to allow the MA substance to interact with the environment (i.e. bacteria, fungi, yeasts, mold, mildew, etc).

The AM material can be applied to any part of the respiratory system in a number of different ways. As a first example, a respiratory part may be extruded using active AM substances or formulated active AM substances in the form of a masterbatch. Examples of extruded respiratory parts are a conduit or part of a respiratory conduit such as a rib of a hose or heated hose; a jacket material of cables or insulation material of wires such as heating wires and signal wires. The AM material can be incorporated over the entire extruded part or in a section of the extruded part. As a second example, a respiratory part may be co-extruded using using active AM substances or formulated active AM substances in the form of a masterbatch. Examples of co-extruded respiratory part are a respiratory conduit or part of a conduit such as a rib of a hose or heated hose, a jacket material of cables or insulation material of wires such as heating wires and signal wires. The AM material can be incorporated over the entire co-extruded part or in a section of the co-extruded part. As a third example, use can be made of injection moulding, low pressure injection or over-moulding using active AM substances or formulated active AM substances in the form of a masterbatch. Examples of injection moulded products are cuffs of hoses, in connectors, in humidifier parts such as humidifier chambers, in filters, Y pieces, . . . . The AM material can be moulded in the entire part or only in a section of the moulded part. As a fourth example, use can be made of in-mould labelling of a component treated with an AM substance to allow cost effective application of the AM substance. As a fifth example all kinds of surface treatments are possible, such as for example:
  a) Printing: AM substances can be printed directly on the substrate
  b) Painting: AM substance can be applied by liquid painting of a lacquer or water based solution or dispersion
  c) Spraying: AM substance can be applied by spraying powder or liquid
  d) Dipping: AM substances can be applied by dipping the substrate into a solution or dispersion of the active AM substance or any formulation thereof.
  d) Gluing
  e) Laser marking
  f) Vacuum deposition
  g) chemical vapor deposition
  h) Physical vapor deposition The conduit as used in any aspect of this invention preferably comprises a hose with at least 4 associated wires, two of them being heating wires for the purpose of heating the breathable gas passing within the conduit, two of them being control wires for the purpose of transmitting signals from measuring device, such as pressure sensors or temperature sensors. A 4 wire circuit has a number of advantages. A first advantage is that the heating and signal circuits do not have to work on a switching basis, but can operate independently and monitor and heat the conduit continuously. In fact, the signal wires are able to monitor continuously the measurements of the at least one sensor and that, at the same time, the heater wires are able to continuously heat the breathable gas passing through the conduit. As a result, such a 4 wire construction allows to respond faster to changes in the conduit compared to switch circuits. Another advantage of such a 4 wire construction is that, since the current may continuously circulate through the at least one sensor, a greater stability of the at least one sensor may be obtained and therefore accuracy can be improved. A third advantage is that such a 4 wire circuit does not need a complex control circuit, which results in reduced costs.

The wires to control such a 4 wire circuit can be associated with the hose of the conduit by any possible way considered suitable by the person skilled in the art. The wires can for instance been located in a hose structure, which can be helically wound, extrusion blowmoulded or extrusion pipe. The wires can also be located down the middle of the respiratory conduit. The wires may also be located externally of the respiratory conduit. In particular, such a 4 wire circuit may for instance be introduced into a conduit obtained with the method according to a second aspect of the invention, comprising a hose with at least one helical wire groove, preferably with two helical wire grooves. In particular, such a 4 wire circuit may be incorporated into a conduit according to a third aspect of the invention, wherein for instance the two heater wires are incorporated into a first helical rib, and the two signal wires are incorporated into a second, parallel extending helical rib.

The hose as used in any aspect of this invention may comprise an inner tube, with a smaller diameter than the hose, and being at least partly attached to an inner face of the hose and provided for holding at least one wire. The at least one wire can be any type of wire, such as a heater wire, signal wire, communication wire, . . . . The tube may be a composite cable, comprising at least one wire, being at least partly attached to an inner face of the hose. The at least one wire may for instance be a NTC or PTC wire. The tube or cable may be attached along the whole of its length or at one or more selected positions. The tube may comprise one ore more wires, for instance the tube may comprise a cable and a signal wire. An advantage of inserting at least one wire in a hose in the above described manner is that a large variety and number of wires can be incorporated. This allows a wide range of sensors to be applied in the conduit, which allow a large range of control possibilities. Preferably, the tube is attached to the inner surface of the hose in a straight pathway, because this results in a reduction of the used material in comparison to the helix route, and thus in a reduction of the material cost. Another advantage is that it is easier to recycle the materials used to make the conduit. If desired a strain relief can be added to the structure. This may be a form of polymer chord which will prevent stretching of the conduit to greater than the design allowance.

The conduit is preferably made of a thermoplastic material, and structured to be flexible and lightweight. The production process to produce the conduit may be any process considered suitable by the person skilled in the art. As an example, but not limited thereto, the following production processes are possible:
(a) Spirally wound from one or more profiles of material.
(b) Spirally wound with an inner web and outer helix. There may be one or more helix forms along the product.
(c) Extruded tube which is reinforced to prevent kinking.
(d) Extrusion blow moulded conduit.
(e) Formed from a tape or similar with a reinforcement material.

Any technique considered suitable by the person skilled in the art may be used to terminate the conduit used in any aspect of the present invention.

Use may for instance be made of low pressure injection (LPI). This technique can be used to terminate the conduit with the required sensors, contact connectors and cuffs to link to other parts of the system. The components would generally be injection moulded parts of compatible plastic materials. The sequence of steps will vary with the number of elements required in the termination. An example would be to add to the conduit a cuff to act as a linking device and a platform for terminals etc. In such a case the component and conduit are placed in a moulding tool. The LPI material is introduced to the desired position to bond the cuff to the conduit. The material can be introduced by low pressure injection or by intrusion moulding machines. The required terminals etc can then be added to the cuff and the assembly completed. In another form the terminal cuff assembly may be completed and then added to the conduit by the LPI process. Such processes are in use by Plastiflex to terminate electrical hose systems for the floorcare market. The process can be used to fill the space within the terminal component to give added security and stability to the connections within. The number of steps will be determined by the degree of complexity of the terminal cuff and the number of functions it is associated with. The process allows the opportunity to use parts of a more complex shape if needed and produced to high tolerance. A wider variety of materials may be chosen. The process is very controlled and gives a lower assembly cost.

An alternative process to terminate the conduit is overmoulding. The end of the conduit is directly overmoulded with a plastic material to bond them, giving a leak free pathway for the fluids to pass along. It also can act as the base or platform to mount the connectors or terminals for the control system. In a next step, the connections for the system can be made. An outer covering which may be an injection moulded component can then be located over the assembly and using the overmould process locked into position onto the conduit terminal assembly. If desired this could be further overmoulded to add other features for example "soft touch". A stress relief feature can be a part of the overmould design. Alternatively the stress relief feature can be a separate moulded part, placed on the conduit and locked to position as a part of the overmould process. The terminal cuff can be designed to allow a range of fittings or contacts to be made in the same structure. This can be used to produce a variety of complexity and control from the same base part. This has a cost benefit to all such variations of the cuff.

Figure 1:
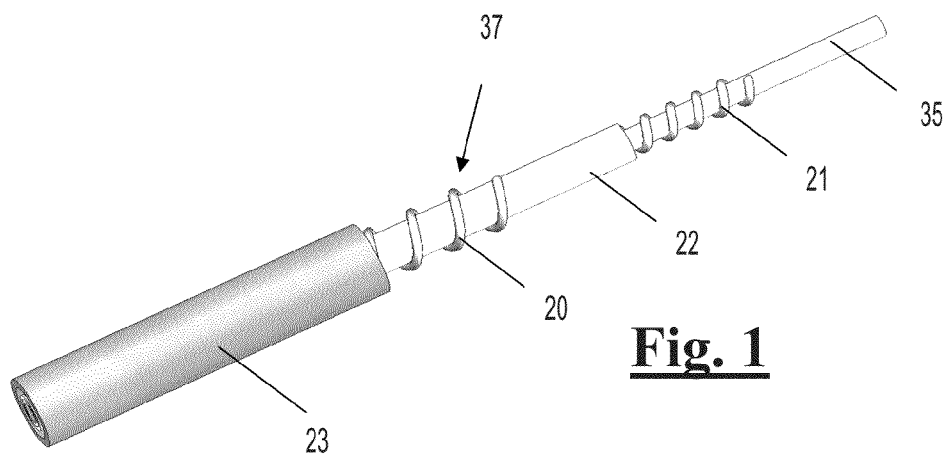
FIG. 1 shows a first embodiment of a heating element of a conduit according to an aspect of the invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

DETAILED DESCRIPTION OF THE INVENTION

The invention will be further elucidated by means of the following description and the appended figures.

FIG. 1 shows a first preferred embodiment of a heating element 37 of a conduit according to an aspect of the invention. The heating element 37 is a coaxial cable construction, which comprises two electrical wires 20, 21, one of which being a heating wire 21, the two electrical wires 20, 21 being separated by a negative temperature coefficient component layer 22. In particular, FIG. 1 shows a coaxial cable construction comprising a heating wire 21 which is helically wound around a textile core 35, a NTC doped polymer coating 22 surrounding the heating wire 21 and a signal wire 20 which is helically wound around the NTC coating 22. The signal wire 20 can be insulated or not. Preferably, an insulation layer 23 is applied around the aforementioned construction as is shown in FIG. 1.

After association of the heating element 37 with a hose, the coaxial wire will allow heating and controlling of the breathable gas flowing through the hose. The coaxial wire heating element 37 as shown in FIG. 1 will use the reduced resistance of the NTC component layer 22 at rising temperature to trigger the power supply to the heating wire. This allows the heating element 37 to detect and minimize overheating inside the hose. As such, the heating element 37 will also allow detecting and minimizing hot spot sections of the heating wire 21. The heating element 37 of the conduit shown in FIG. 1 preferably has the following further properties/advantages: low power/wattage, thermostatic control, UL/CSA certified, low cost option, smallest overall diameter, 105° C. continuous rated PVC, hot spot detection, overall temperature monitoring.

Figure 2:
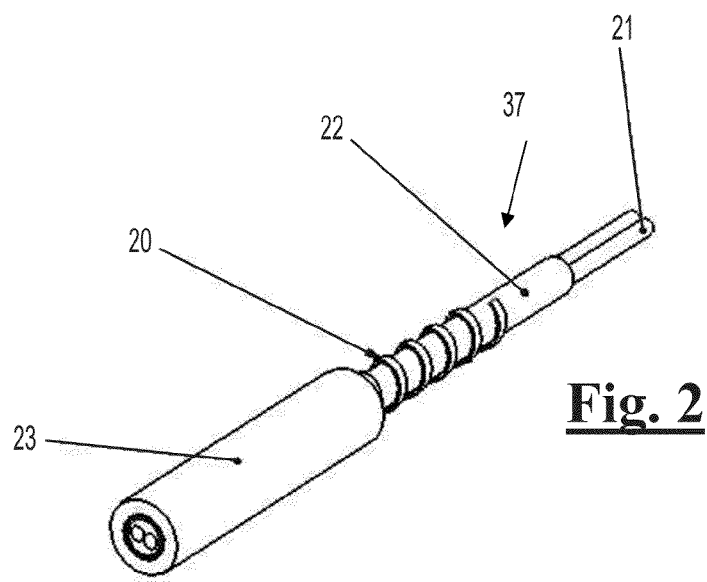
FIG. 2 shows a second embodiment of a heating element of a conduit according to an aspect of the invention.

FIG. 2 shows a second preferred embodiment of the heating element 37 provided in the conduit according to an aspect of the invention. The heating element 37 is a coaxial cable construction. The construction comprises two heating wires 21 in the core of the construction which extend in longitudinal direction of the hose. Each of the heating wires 21 has a ceramic coating for insulation. The heating wires 21 are electrically connected to each other at one end, and at the other end they are connected to the same power supply. A NTC coating layer 22 surrounds the heating wires 21. A signal wire 20 is applied around the coating layer 22. In FIG. 2, the signal wire 20 is helically wound around the coating layer, but it may be applied in any other way considered suitable by the person skilled in the art. The signal wire 20 can be insulated or not. Preferably, an insulation layer 23 is applied around the aforementioned construction as is shown in FIG. 2. The outer insulation layer allows the coaxial wire heating element 37 to be in direct contact with the breathable gas within the hose without causing short circuit.

In addition to the advantages of the heating element shown in FIG. 1, the heating element shown in FIG. 2 has the advantage that only one cable has to be incorporated into the hose for heating the breathable gas within the conduit. In general, in order to provide a closed electrical circuit, there are two wires in the conduit, one wire going to the patient interface and one going back to the flow generator. The co-axial cable configuration shown in FIG. 2 offers a more compact heating element, in which the two wires are incorporated into one single cable which can be incorporated as a single cable into the hose.

Optionally, the heating elements 37 shown in FIGS. 1 and 2 may comprise a PTC coating layer instead of a NTC coating layer.

Figure 3:
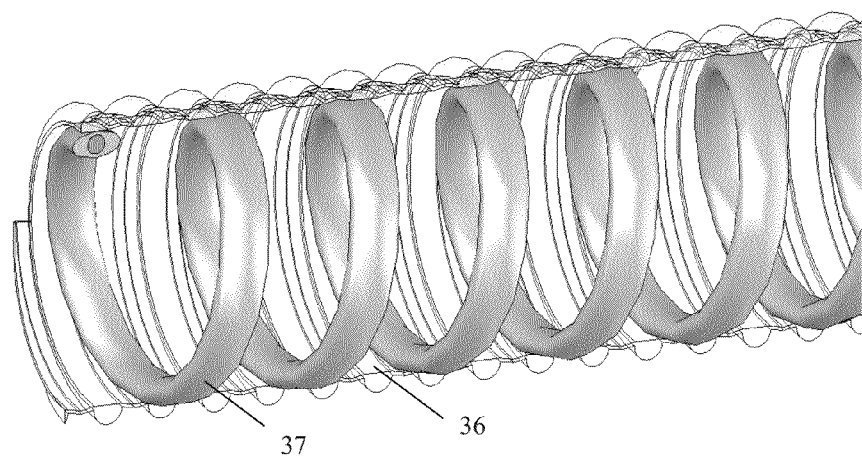
FIG. 3 shows an embodiment of a conduit according to an aspect of the invention, comprising a coaxial wire heating element which is wound like a spring and removably inserted into the conduit.

The cross section of a heating cable, such as for instance the coaxial cable construction as shown in FIGS. 1 and 2, can have any shape considered suitable by the person skilled in the art, such as round or oval. Preferably, a heating cable has an elliptical diameter as is shown in FIG. 3. Such an aerodynamic wire structure offers a number of different advantages. It improves breathing pressure drop, minimizes air turbulence, minimizes moisture buildup and reduces bacterial build up. It allows a spring wounded heating cable to be torqued against the hoses inner wall. It further allows improved heat dispersion into the wall of the hose through a greater contact area. It further improves aerodynamics with a profiled shape and location against the hose wall. The elliptical shape further allows the formation of rod into spring characteristics.

Cable constructions, as for instance coaxial cable constructions as shown in FIGS. 1 and 2 allow for an easy and compact insertion of the heating element into the hose. The insertion can be done by any method considered suitable by the person skilled in the art. The coaxial cable construction can for instance be inserted into an internal or external wall, into an internal or external rib of the hose, into an internal or external groove of the wall, loosely provided within the hose, would like a spring, . . . .

FIG. 3 shows a coaxial wire heating element 37 which is wound like a spring and removably inserted into a hose 36. The wounding of the coaxial wire heating element 37 as a spring and the insertion into the hose 36 can be done in any way considered suitable by the person skilled in the art. To insert the coaxial wire heating element 37 into the hose 36, the wire 37 is for instance connected to a spider rod and is inserted in the hose 36 by using a heavy bullet or ball or weight device in any form. The diameter or thickness of the bullet or weight is smaller than the internal diameter of the conduit. The bullet is connected to a locater wire and dropped into the hose at one end. By falling through the hose using gravity, the locator wire is pulled through leaving the spider rod exposed at the other end of the hose. The spider rod is then assembled with a spider and with the coaxial wire heating system. The spider rod and heating element 37 are then pulled into the correct position. At that moment, the heating element 37 is assembled in the conduit. Applying a slight tortional force, the wire 37 behaving as a spring, is brought into position, making contact with the conduit inner wall. The wire is then locked into position using the spider keeping one end of the spring wire in position. The spider rod is then disengaged from the location spider by rotating the spider rod to disengage location pegs. The heating wire 37 is then assembled in the conduit. This technique can be used to insert any type of wire into the conduit, for instance a heater wire, signal wire, combined cable construction, . . . .

The construction shown in FIG. 3 has the advantage that the heating element 37 is removably inserted into the hose. The heating element 37 can thus be re-used and does not have to be thrown away together with the hose, which leads to lower replacement costs. This is in particular of importance for hoses which have to be periodically replaced, such as for example heated respiratory hoses. Other advantages of the construction shown in FIG. 3 are that it contributes to improved conductivity between the coaxial wire heated element 37 and the hose wall and that it improves heat dispersion within the hose and energy use of the heating element. The heating element as shown in FIG. 3 may comprise a NTC or a PTC component.

Figure 4:
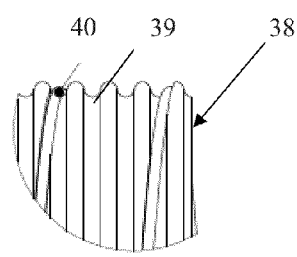
FIG. 4 shows a conduit, which is manufactured according to an aspect of the invention, comprising a blowmoulded tube with a corrugated wall with a helical wire groove on the exterior surface of the tube.

FIG. 4 shows a conduit which is manufactured according to an aspect of the invention. The conduit comprises a blow-moulded tube 38 which comprises a corrugated wall 39. The corrugated wall 39 of the tube 38 comprises a number of corrugations. The tube 38 further comprises a helical wire groove 40 on the exterior surface of the tube. A wire for heating or communication purposes is inserted in the wire groove 40. When a heating wire is for instance inserted in the wire groove 40, this configuration contributes to improved conductivity between the heating wire and the tube wall 39 and it improves heat dispersion within the tube and energy use of the heating wire. Because these helical wire grooves 40 can be created directly from the extrusion machines, this construction offers a fast and cost-efficient solution to insert heating wires in a hose. Moreover, this construction has the advantage that the helical wire groove 40 can be provided at whatever possible pitch. Preferably, the pitch of the helical wire groove 40 is larger than the hose pitch of the corrugations 39 of the hose itself, such that less heater wire is needed to provide the same length of the hose. This results in a reduction of costs of the heated conduit.

Figure 5:
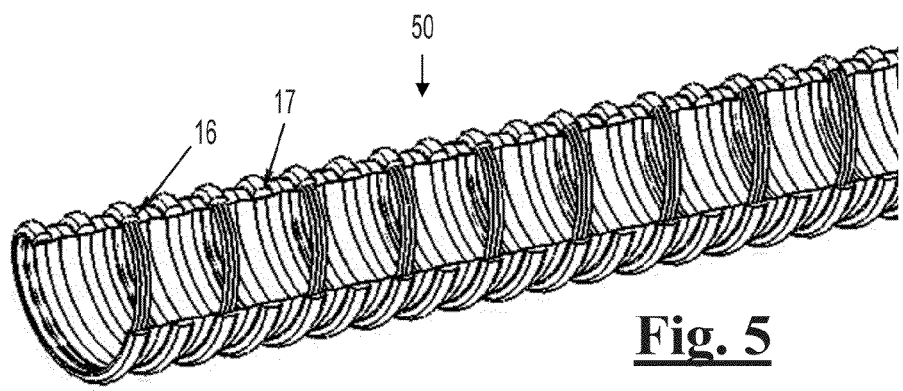
FIG. 5 shows a conduit, comprising a double pitch hose, for use in a respiratory system according to an aspect of the invention.

FIG. 5 shows a conduit for use in a respiratory system for supplying a breathable gas from a flow generator to a patient interface. The conduit shown in FIG. 5 comprises a double pitch hose 50, which comprises two parallel extending helical ribs 16, 17 at an outer surface of the hose 50. In FIG. 5 only one of the ribs comprises a wire. Alternatively, both ribs may comprise one or more wires. This wire may be a heater wire, a communication wire, or a combined cable construction as shown in FIGS. 1 and 2 or any other wire or cable. Conduits like the one of FIG. 5 can be made by a blowmoulding process or a helical winding process.

Figure 6:
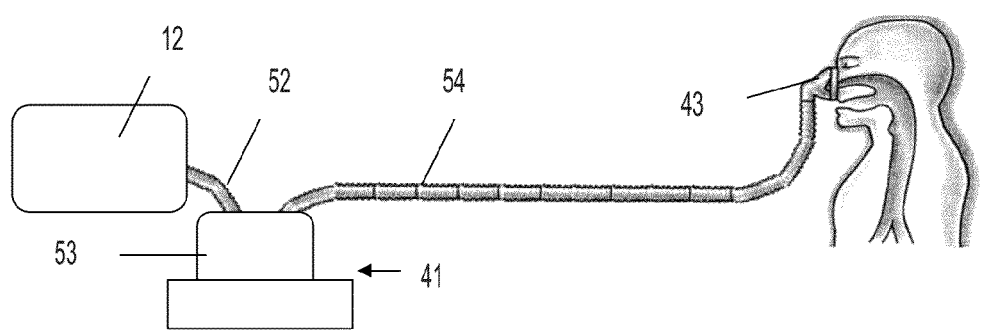
FIG. 6 shows a first embodiment of the respiratory system according to an aspect of the invention.

FIG. 6 shows a first preferred embodiment of the respiratory system according to a fourth aspect of the invention. The respiratory system comprises a flow generator 12, a humidifier system 41 for heating and humidifying a breathable gas received from the flow generator 12 and a conduit 54 for supplying a breathable gas from the humidifier system 41 to a patient interface 43. The humidifier system 41 comprises an inlet for taking in a breathable gas and a humidification chamber 53 connected to the inlet and provided for heating and humidifying the breathable gas before delivery to the conduit 54. The flow generator 12 is connected with the inlet of the humidification chamber 53 through a heated inlet hose 52, which functions as a pre-conditioning system. An inlet heating element is associated with the inlet hose 52 and pre-heats the breathable air before entry into the humidification chamber 53. The flow generator 12 may also be a CPAP unit with an integrated humidifier and heating system, which is here used as the pre-conditioning system. The amount of heating is under control of a controller and may be determined based on a measurement of ambient air characteristics or characteristics of the breathable gas in the inlet, for instance a dewpoint measurement.

Figure 7:
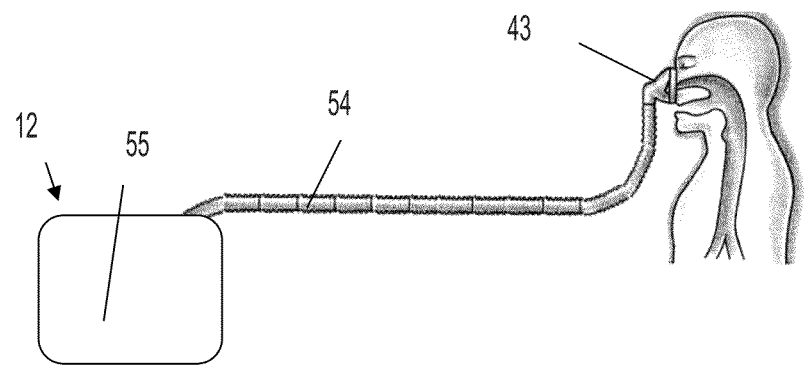
FIG. 7 shows a second embodiment of the respiratory system according to an aspect of the invention.

FIG. 7 shows a second preferred embodiment of the respiratory system according to a fourth aspect of the invention. The respiratory system comprises a flow generator 12 with an integrated humidifier system 55 for heating and humidifying a breathable gas and a conduit for supplying a breathable gas from the humidifier system 55 to a patient interface 43. The respiratory system comprises a pre-conditioning system for pre-conditioning the breathable gas before entry into the flow generator. This pre-conditioning system is here integrated into the CPAP unit and may comprise a temperature control system for influencing the temperature of the breathable gas or a humidity control system for influencing the humidity of the breathable gas before entry into the flow generator and the subsequent main humidifier of the system. The amount of heating is under control of a controller and may be determined based on a measurement of ambient air characteristics or characteristics of the breathable gas. Optionally, the flow generator 12 with the integrated humidifier system and pre-conditioning system 55 can be used itself as a pre-conditioning system for heating and humidifying the breathable gas before entry into a second humidifier system (not shown).

In the respiratory systems of FIGS. 6 and 7 also a fifth aspect of the invention is applied, namely to control of the temperature and humidity levels of the air traveling from the humidifier chamber to the patient on the basis of a dewpoint measurement in this part of the conduit 54, preferably at least at the patient interface.

Preferably, in order to further optimize the efficiency of the humidifier system of the respiratory system, the temperature of the water in the reservoir of the humidification chamber is set sufficiently high to generate enough heat capacity of the water enabling efficient energy transfer to moisturize the air flow and to heat up the air flow (if necessary). The temperature of the water in the reservoir of the humidification chamber is preferably controlled. The control can for instance be done based on the ambient air conditions or based on dewpoint measurement of the breathable gas.

Optionally, in order to further optimize moisture and heat transfer to the breathable gas, the construction of the reservoir and humidification chamber of the humidifier system may be as follows:

Reservoir and humidification chamber enabling longer residence time of the transported air using baffles Reservoir and humidification chamber having headspace volume more than 100 ml Reservoir and humidification chamber with air inlet that creates turbulence to maximize contact surface between air and water Reservoir and humidification chamber that can be heated to temperatures between 5° C. and 100° C.

Humidifier system has overheating control

Humidifier system allows maximizing the humidity transfer into the outlet air flow Humidifier system allows the inlet air to percolate through the water in the reservoir Humidifier system uses ultrasonic systems to generate vapor droplets.

Preferably, in order to further increase the performance of a humidifier system, the water reservoir of the humidifier system is thermally insulated. As a result, the performance of the humidifier system can be made less dependant on the ambient conditions and is able to perform better in challenged conditions. As such, even at restricted power consumption, the humidifier is able to generate more humidity compared to a humidifier without insulated tank, as can be seen from table 1. In table 1, $T_{waterbath}$ is the temperature of the water in the humidification chamber, $Td_{ambient}$ is the ambient air temperature and $Td_{output}$ is the dewpoint temperature of the breathable air leaving the humidification chamber, which is a measure for humidity level of the breathable air.

| Tank | $T_{waterbath}$ | $Td_{ambient}$ | $Td_{output}$ |
|---|---|---|---|
| Without insulation | 55° C. | 17° C. | 21.0° C. |
| With insulation | 69° C. | 17° C. | 24.5° C. |

In case the humidifier system is integrated in a flow generator, the power consumption of the total system might be restricted. An insulated humidifier chamber will help to save energy and effective use of power to maximize the humidity output of the system.

The insulation of the humidifier system can be done with any means considered suitable by the person skilled in the art. The humidification chamber may be for instance a double walled chamber construction. The cavity between the two wall can either be vacuum, air or filled with an insulating material, for instance with foam. A double walled chamber construction in which the cavity is air filled and allows the air coming from the flow generator to pass through prior to passing over the headspace of the water surface is preferred. The humidification chamber may comprise an insulation layer in the form of a material attached, glued, connected to the water chamber. The insulation material can be a foamed material, a textile construction.

Test results disclosed hereunder prove that neither of the tested systems, when operated under normal conditions and challenged conditions are able to deliver the optimal setting for humidity and temperature but stay well below this optimal setting especially for absolute humidity. The test results prove that the efficiency of a humidifier in delivering warm and moisturized breathable gas to a patient can be significantly improved with a respiratory system according to a fourth and/or fifth aspect of the invention.

Test Results

1. Benchmark Testing:

F&P HC 604: CPAP with integrated heated humidifier and Thermosmart® technology.

Settings:

Pressure: 10 cm H20

Variable parameter: heating of the heated hose from 0 (Off) to 10

Results and Discussion

The F&P machine was tested in different ambient conditions.

Tw=temperature of water in reservoir (° C.)

T=temperature of outlet air (° C.) measured with Hanna-Instruments Thermo-hygrometer HI9565

Td=dewpoint of outlet air (° C.) measured with Hanna-Instruments Thermo-hygrometer HI 9565

| Setting Heated Hose | 1 T ambient = 13-14° C. Td ambient = 9-9.5° C. | | | 2 T ambient = 21° C. Td ambient = 9-9.5° C. | | | 3 T ambient = 22-23° C. Td ambient = 9-9.5° C. | | |
|---|---|---|---|---|---|---|---|---|---|
| | Tw | T | Td | Tw | T | Td | Tw | T | Td |
| 0 | 53-54 | 19.8 | 19.5 | 53 | 25 | 21.1 | 57-58 | 27.4 | 20.7 |
| 5 | 53-54 | 21 | 20 | 55 | 25.8 | 21.8 | | | |
| 10 | 53-54 | 23.1 | 20 | 56 | 27.5 | 21.8 | 58 | 30.7 | 21.1 |

Column 1:

At an ambient temperature of 13-14° C., the HH generated an airflow with a dewpoint of 19.5° C. (eq. to 16.8 mg water/l air). At these extreme conditions, condensation was visible in the unheated hose. Ref. condensation appears when the temperature of the outlet air equals the dewpoint of the outlet air.

When the T-setting on the heated hose was increased, the temperature of the outlet air significantly increased from 19.8° C. to 23° C. This temperature increase was able to remove the condensate (T outlet air >T dewpoint). The temperature of the outlet air did not reach 30° C.

The temperature increase due to heating the hose did not have an impact on the dewpoint of the outlet air. This is logical since the dewpoint of the outlet air is determined by the efficiency of the HH.

Columns 2 and 3:

The same effects were observed in the experiments summarized in columns 2 and 3. By activating the hose heating system, the temperature of the outlet air is significantly increased. The dewpoint of the outlet air is unaffected (note in column 2: the slight increase in dewpoint is due to the increase in the temperature of the waterbath of the HH).

Conclusion

The heated hose of the F&P machine significantly increases the temperature of the outlet air. At ambient conditions around 22-23° C., the outlet air temperature can reach the desired 30° C.

The heated hose of the F&P machine is able to avoid condensation, even at extreme conditions of ambient temperatures around 13-14° C. Under these conditions, an outlet air temperature of 30° C. was not achieved. It is yet not clear whether the system will be able to avoid condensation at ambient temperatures of 5° C. (as mentioned in the technical specifications).

From these experiments, it seems that the F&P HH with heated hose is not able to deliver the 30 mg water/liter of air (equivalent to a dewpoint of around 30° C.), neither in comfortable ambient conditions of 21-23° C., neither in challenged conditions (13-14° C.). The maximum dewpoint was around 21-22° C. or equivalent to 18.3-19.3 mg water/liter air).

2. Test Setup According to the Invention

The experimental setup comprises:
A Breas i-Sleep 10 CPAP unit connected with a Breas Heated Humidifier HA 50 via a CPAP inlet hose of 1.8 meter with heating element.
A CPAP outlet hose of 1.8 meter with heating element.
Settings of the CPAP unit:
Pressure: 10 cm H20
Settings of the HH:
Heating from 0 to 9
Experiment 1:
Air flow: 10

| Setting | Heating Inlet | Heatting Outlet | Other | T ambient = 13-14° C. Td ambient = 9-9.5° C. | | |
|---|---|---|---|---|---|---|
| HH | Hose | hose | mofications | T w | T | Td |
| 1 | 9 | off | on | | 45 | 25.4 | 18.3 |
| 2 | 9 | on | on | | 45 | 25.9 | 21.4 |
| 3 | 9 | on | on | with plug in | 45 | 28.3 | 24.4 |
| 4 | 5 | on | on | with plug in | 38.6 | 27.1 | 21.6 |

Line 1-Line 2: Effect of Heating the Inlet Air:

When the inlet air was not heated, the dewpoint of the outlet air is 18.3° C. (equivalent to 15.6 mg water/liter air). With the heating system in the inlet hose on, the dewpoint is increased to 21.4° C. or 18.7 mg/l. This is an increase of 20% in vapor content. Note that heating the inlet air does not have a significant effect on the outlet air temperature.

Line 2-Line 3: Effect of Air Turbulence on Water Surface

A plug was mounted on the inlet on the inside of the HH in order to create turbulence on the water surface in the reservoir. The plug is also expected to have an effect on the air flow speed (air flow reduction).

As a result of mounting the plug, another 3° C. dewpoint increase was noticed. There also seemed to be a better heat transfer from the hot water in the reservoir to the air flow (T outlet air also increased with >2° C.). Under the same conditions, a sufficiently higher dewpoint was reached compared to the F&P machine.

Line 3-Line 4: Effect of Water Bath Temperature

Decreasing the water bath temperature from 45° C. to 38-39° C. resulted in a drop in dewpoint of 3° C. indicating that the water has a reduced heat capacity. Energy in transferred in heating the outlet air and moisturizing the air flow. By reducing the water bath temperature, moisturizing the outlet air is less efficient. The effect on the outlet air temperature is minimized due to the heating of the outlet air in the outlet hose.

Conclusion:

By introducing heated air into the HH (e.g. via a heating element in the inlet hose), the capacity of the inlet air to hold moisture is significantly increased. By heating up the cold air, energy extraction for heating up the air flow from the water bath is minimized so more energy is available for vaporization. The result is a better efficiency of the HH.

By creating turbulence on the water surface and increasing the residence time in the HH (by slowing down air flow), more humidity and heat is transferred to the outlet air flow resulting in a higher dewpoint and outlet air temperature.

By increasing the temperature of the HH, the heat capacity increases enabling more efficient humidification of the outlet air.

Experiment 2
Air flow: 10

| Setting | Heating Inlet | Heatting Outlet | Other | T ambient = 13-14° C. Td ambient = 9-9.5° C. | | |
|---|---|---|---|---|---|---|
| HH | Hose | hose | mofications | Tw | T | Td |
| 9 | on | on | | 48 | 34.7 | 22.2 |
| 9 | on | on | with baffles | 48 | 35.8 | 25.2 |
| 9 | on | on | with plug + baffles | 48 | 36.5 | 31.3 |

Confirmation of Effect of Increased Residence Time and Water Surface Turbulence:

Two baffles were introduced in the HH to force the air to circulate over the heated water surface: increase in dewpoint of 3° C. Adding the plug (restricted air flow+turbulence on water surface) resulted in another 6° C. increase in dewpoint.

Experiment 3
Air flow: 10

| Setting | Heating Inlet | Heatting Outlet | Other | T ambient = 23° C. Td ambient = 9-10° C. | | |
|---|---|---|---|---|---|---|
| HH | Hose | hose | mofications | Tw | T | Td |
| 9 | off | off | with baffles | 48 | 29.3 | 22 |
| 9 | on | off | with baffles | 48 | 29.2 | 23 |
| 9 | on | on | with baffles | 48 | 36.2 | 22.9 |

Confirmation of effect of heated inlet air: dewpoint increase of 1° C. This increase is significant but less explicit when compared to more extreme ambient temperature of 13-14° C.

Very obvious effect of heating the outlet air in the outlet hose: temperature increased with 7° C.

Experiment 4
Air flow: 10

| Setting | Heating Inlet | Heatting Outlet | Other | T ambient = 22-23° C. Td ambient = 9-9.5° C. | | |
|---|---|---|---|---|---|---|
| HH | Hose | hose | mofications | Tw | T | Td |
| 9 | off | on | | 46 | 32.2 | 20.4 |
| 9 | on | off | | 46 | 27.4 | 22.5 |

Confirmation of effect of heating the inlet air: significant dewpoint increase.

Turning heating of outlet air off results in significant decrease of outlet air temperature.

Experiment 5
Air flow: 20

| | Setting | Heating Inlet Hose | Heatting Outlet hose | Other mofifications | T ambient = 20° C. Td ambient = 12° C. | | |
|---|---|---|---|---|---|---|---|
| | HH | Hose | hose | mofifications | Tw | T | Td |
| 1 | 9 | on | on | with baffles | 48 | 29.5 | 20.5 |
| 2 | 9 | on | on | with baffles | 54 | 30.3 | 23.6 |

Confirmation of the effect of increased water bath temperature: water bath temperature increase results in higher heat capacity of the water and hence in a higher dewpoint and temperature of the outlet air.

Figure 8:
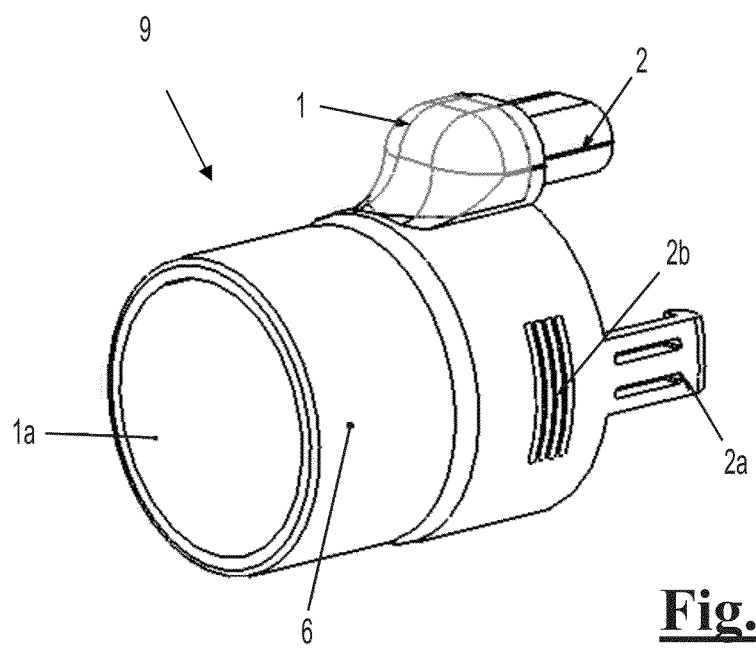
FIGS. 8 and 9 respectively show a front and rear view of the cuff for a conduit according to a sixth aspect of the invention.
Figure 9:
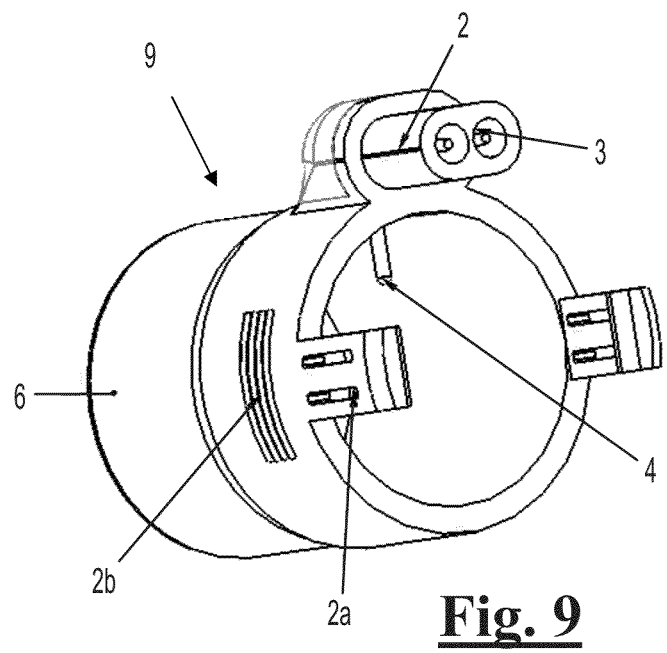

FIGS. 8 and 9 respectively show a front and rear view of the cuff 9 according to a sixth aspect of the invention. The cuff 9 comprises a passage for a breathable gas flowing in the respiratory system. The cuff shown in FIGS. 8 and 9 comprises an integrated sensor 4 for measuring respiratory care parameters of the breathable gas. The integrated sensor 4 is located in the passage of the cuff 9. The sensor 4 is connected to electrical pins 3 via internal wiring. The cuff 9 shown in FIGS. 8 and 9 can be connected directly onto a part of the respiratory system or can be connected to a connection cuff of any part of the respiratory system, for instance with the aid of a cuff fitting 6. FIG. 9 shows for instance an electrical male housing 2 for fitting into a female conduit cuff. Electrical pins 3 are located within the electrical male housing 2. As such, the electrical pins 3 of the cuff 9, may connect directly to the internal wiring of for instance the hose, or may connect to corresponding electrical pins of a connection cuff of the hose. The cuff 9 as shown in FIGS. 8 and 9 comprises a cuff housing 1a which is designed to fit the standard ISO tapper fitting. Shown on the side of the cuff are grip features 2b to assist the user when connecting or disconnecting the cuff via securing clips 2a. FIGS. 8 and 9 further show the overmould 1, which secures internally the sensor and electrical connecting pins.

The cuff 9 may comprise multiple sensors 4. The sensors 4 may be provided for measuring any respiratory care parameters of the breathable gas, such as temperature, humidity, pressure, stress, strain, oxygen concentration, CO2 concentration, air flow speed and any other parameters considered suitable by the person skilled in the art.

The cuff 9 may comprise other modules, such as communication modules which make use of radio frequency, bluetooth, infra-red, microwave, fibre optics or any other like technologies. The sensors and modules can communicate with their appropriate devices such as individual controllers for heating, flow generators, humidifiers or any other associated equipment for communication.

The cuff 9 can transfer information via hard wiring located within the structure of the respiratory conduit. The wiring for the heating and/or information transfer can be located within the respiratory conduit or externally of the respiratory conduit. Preferably, the wiring is located inside of the respiratory system. This has the advantage that the user cannot tangle the wiring and cause damage to the wiring or sensors.

The cuff connection is preferably designed for connecting directly onto the respiratory conduit. Preferably, the cuff 9 comprises a securing system 2a to prevent the cuff 9 from accidentally disengaging from the respiratory conduit. The signal transfer of the at least one sensor 4 may be done by electrical harness pins 3 engaging male and female connectors respectively located on the parts of the respiratory system and cuff 9. This reduces the risk to incorrect installation of the wiring or sensors within the conduit.

The cuff 9 can be used to act as a through conduit where additional respiratory conduits can be attached to. Additional sensors may be externally added to the cuff 9 and connected to the cuff 9. The additional sensors may then utilise the wiring connected to the cuff 9.

A respiratory system can comprise more than one cuff, for instance one at the entry of a conduit and one at the end of a conduit to measure differences between input and output.

Sensors within the cuff 9 can be made form a variety of materials. The need for different materials can be for system response times, durability, sterilization and accuracy. An example of this can be in a hospital environment where patient response and accuracy of measurement maybe clinically more critical than in a home therapy environment. Sterilization in hospitals places higher demands than those in the home environment, and the sensor and housing and connectors must with stand autoclaving.

Preferably, the cuff 9 is adapted for being fitted to hoses of multiple sizes. This means for example that the user can utilize smaller bore hose's closer to the patient, and this pressure drop down the smaller hose section can be balanced by utilizing larger bore conduit near the flow generator/humidifier.

The cuff 9 can be manufactured using a number of different techniques, including overmoulding, intrusion moulding and or injection moulding. The overmoulding technique can be used the provided different material configurations for example the bore of the cuff can be made for a harder material allowing easier connection to associated equipment. The outer overmould 1 can be made from a soft touch material to enable easier handling by the patient. Sensors 4 used in the construction for the purpose of the temperature measurement, can be any type of sensors considered suitable by the person skilled in the art, such as NTC or PTC components.

Figure 10:
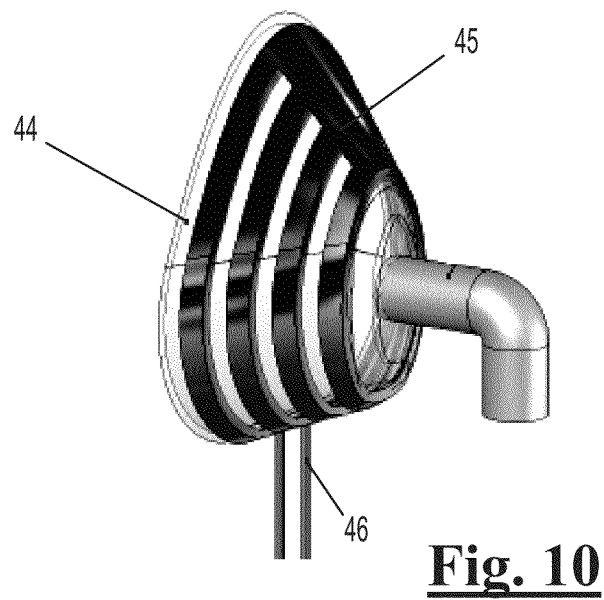
FIG. 10 shows a first embodiment of a respiratory mask according to an aspect of the invention comprising a heating system for heating the breathable gas inside the mask.

FIG. 10 shows a first preferred embodiment of the respiratory mask 44 according to an aspect of the invention. The respiratory mask comprises a heating system 45 provided for heating the breathable gas inside the mask. The heating system 45 comprises a heater mesh attached to the outside of the mask. Any other type of heating system may be used and any other location of the heating system on the mask is possible. The heater mesh is connected with connector wires 46 to a controller for controlling, which controls the heater mesh. The respiratory mask 44 shown in FIG. 10 has a single wall, but may comprise a double wall, which may further reduce the occurrence of condensation inside the mask.

Figure 11A:
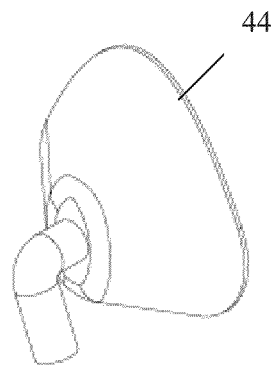
FIGS. 11a and 11b show a second embodiment of a respiratory mask according to an aspect of the invention, comprising a double wall.
Figure 11B:
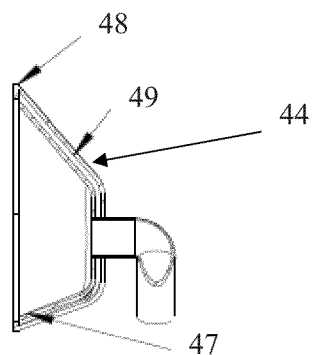

FIGS. 11a and 11b show a second preferred embodiment of the respiratory mask 44 according to an aspect of the invention. The respiratory mask comprises a double wall formed by an outer shell 48 and an inner shell 47. The outer and inner shell enclose a sealed cavity 49.

Figure 12:
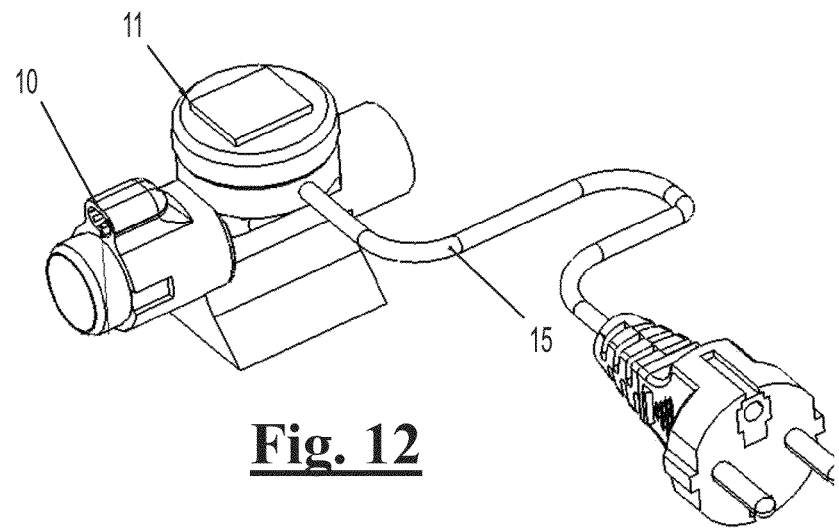
FIG. 12 shows an embodiment of a controller for use in a modular respiratory system according to an aspect of the invention.

FIG. 12 shows a preferred embodiment of a controller 11 for use in a modular respiratory system. The controller comprises a cable 15 to be connected to a power supply. The controller comprises a passage for a breathable gas flowing in the respiratory system and at least one integrated sensor in the passage for measuring respiratory care parameters of the breathable gas. The at least one sensor is connected to electrical pins 10 via internal wiring. The controller comprises a click-on part by which it is removably connectable to a part of the respiratory system.

The controller 11 is an electronic device which is designed in such a way that it can be powered by any number of power sources and can be adapted to work with all common power supplies by means of an appropriate transformer, e.g. a transformer which can be switched according to the mains voltage of the power network where the controller is used. If required, the controller 11 can for instance also be powered by means of a battery.

The controller 11 is preferably provided with a user interface 5 which allows adjusting any settings as required by the patient, such as temperature and/or humidity of the gas delivered to the mask. The user can adjust the settings either by hard wiring communication or via wireless technology. The controller 11 can be provided for collecting patient or monitoring information that can be continuously downloaded as stream data relating to patient comfort, sensor measurements, patient usage, technical diagnosis and patient personal data. This information can, if required, be stored in the controller 11 and can be downloaded at any appropriate time. The controller can have the facility to inform the user of relevant alarms as desired.

The controller 11 can be provided for reading information from associated sensors of the hose system required for patient care. Such sensors could for instance be used to measure temperature, pressure, time, flow rates, gas mixture levels, ambient temperatures and/or the dewpoint of the air in the hose system. The controller 11 can for example use ambient tracking, such as the ambient temperature, to control fluid temperature. The controller 11 can communicate with sensors via means of hard wiring, fibre optics, polymer resistance changes, a mechanical interface or any other means known to the person skilled in the art. The controller 11 can be a local controller, i.e. a controller which is close to the hose system, or a remote controller, i.e. a controller which is placed on a distance from the hose system.

The controller 11 is preferably designed in such a way that it can connect to any part of the respiratory system. The controller can be connected to one hose or to multiple hoses. These hoses can connect to the entrance and exit of the controller, and can then be connected to the exit of the humidifier and the patient mask as required. The controller 11 can be connected directly to the humidifier 41/flow generator 12 exit, after which a respiratory conduit transfers the gas flow to the patient. The controller 11 can control the humidity levels and temperature levels for the patient. This can be done by a number of means. Firstly the controller 11 can measure the exit temperature and humidity levels. This will allow the controller 11 to control the temperature to allow the gas to maintain a 100% humidity level. The controller 11 can control the patient temperature. It is possible for the patient to control their temperature via the controller key pad or via a human machine interface. The controller 11 can be linked into the humidifier and this provides the added benefit of supplying the patient with ideal conditions. If the controller 11 is linked into the humidifier 41 the patient can control the humidity levels and temperature levels in combination.

The controller 11 may comprise multiple sensors. The sensors may be provided for measuring any respiratory care parameters of the breathable gas, such as temperature, humidity, pressure, stress, strain, oxygen concentration, CO2 concentration, air flow speed and any other parameters considered suitable by the person skilled in the art. The controller 11 may comprise other modules, such as communication modules which make use of radio frequency, blue tooth, infra-red, microwave, fibre optics or any other like technologies.

The controller 11 can utilise wireless technology to communicate with other sensors/units. This technology can include radio, Bluetooth, infrared etc.

The controller 11 can determine alarm conditions. These conditions could include incorrect installation of the respiratory conduit. It could include hot spot detection in cooperation with additional technologies such as NTC/PTC wiring.

The controller 11 could determine if the hose has been blocked. This is done by measuring a number of parameters such as input and exit temperatures, air flow etc.

Figure 13:
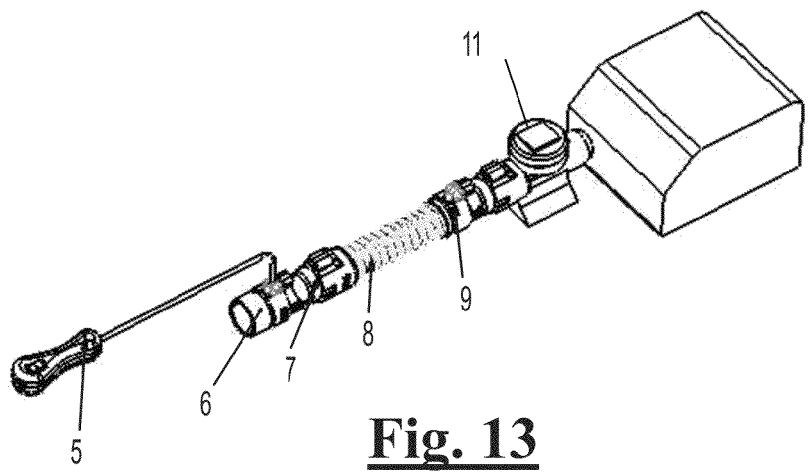
FIG. 13 shows the embodiment of the controller of FIG. 12, applied in a modular respiratory system.

FIG. 13 shows the preferred embodiment of the controller 11 of FIG. 12 applied in a modular respiratory system. In FIG. 13 the controller 11 is directly connected with one end to the flow generator. FIG. 13 further shows the controller being connected with another end to a conduit cuff 9, which is connected to a conduit, the conduit being connected to a cuff 6 with the aid of a connection cuff 7, the cuff 6 being connected to a human machine interface 5.

Figure 14:
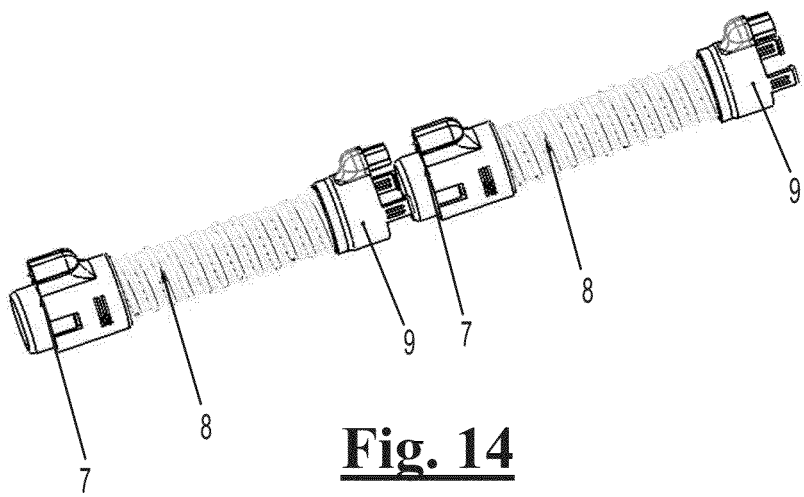
FIG. 14 shows two interconnecting conduits being removably connectable to each other.

FIG. 14 shows two interconnecting conduits 8 being removably connectable to each other. Each of the interconnecting conduits 8 comprises a male fitting 7 which is removably connectable to a female fitting 9 of another interconnecting conduit. The interconnecting conduits 8 may contain electrical wires, provided for heating or communication purposes.

The interconnecting conduit sections 8 may contain male and female fittings at either end, provided to allow electrical connection to additional conduits. The male and female fittings can connect to controllers 11 used for the purpose of controlling, to flow generators 12, humidifiers 41 and any other associated equipment. The male and female fittings are designed to eliminate the risk of incorrect installation. The fittings can be designed in such a way as to allow swivel connections similar to those used in the vacuum cleaner industry. The fittings of the interconnecting conduit can connect to cuffs. This has the advantage of isolating the cuff from the hose structure. It is normally the case that damage occurs to the hose and not to the fitting. Manufacturers have tried to reduce the risk of damage by introducing strain relief, but inevitably damage does occur to the hose. Using the interconnecting conduit sections 8 means that the user does not need to replace the system as a whole and only needs to replace the damaged section.

Using the interconnecting conduit sections 8 means that the conduit system as a whole can contain different conduit constructions as required. For example the first section can be made from the cheaper blowmoulding type construction, and nearer the patient a spiral section can be used. This has the sole purpose of giving the user the hose characteristics where they need them. Larger bore conduits can for example be used near the flow generator/humidifier and smaller bore hoses can be used closer to the patient. Using smaller bore lighter weight and more flexible conduits near the patient end will improve patient comfort. In conjunction with the conduit sections the pressure losses down the complete system can be balanced to minimise pressure losses. The sections can contain valves at intermediary points along the conduit construction. These valves for instance have the purpose of isolating backpressure and reducing the risk of infection travelling back down the conduit.

The interconnection conduits wiring for the heating/information transfer can be located within the hose structure, and this hose structure can be helically wound, extrusion blowmoulded or extrusion pipe. The wires can also be located down the middle of the respiratory conduit. The wires may be located externally of the respiratory conduit.

The interconnecting conduit sections 8 can connect directly onto the respiratory mask and can connect directly onto the humidifier/flow generator as required. Using the standard male female cuffs at each end of the conduits allows different hose constructions to be used with standard cuffs. It allows the user to select a variety of hoses for different purposes to be used. It allows the user to have different heating configuration over the hose length.

Figure 15:
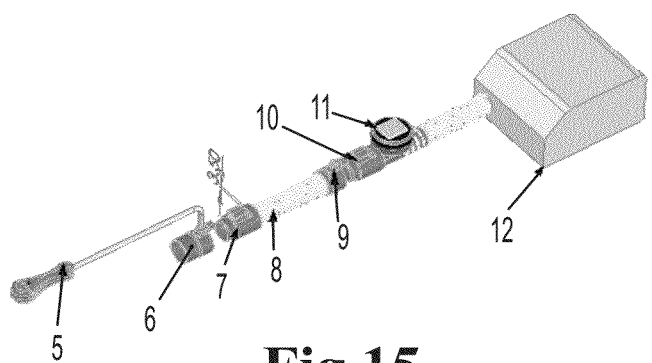
FIG. 15 shows a human machine interface provided to control respiratory care parameters.

FIG. 15 shows a human machine interface 5 provided to control respiratory care parameters. The human machine interface 5 shown in FIG. 15 is removably connected to a cuff 6 via a wire. The cuff 6 is removably connected to a female connection cuff 7 of a conduit. The connection cuff 7 comprises electrical mating pins for connecting to the internal and/or external and/or integrated conduit wiring. This internal and/or external and/or integrated conduit wiring is then passed over the conduit to male connection cuff 9 of the conduit, at the other end of the conduit. The male connection cuff has male pins, which are designed to connect to any other respiratory part of the respiratory system, such as for instance another female connection cuff or a controller.

The HMI 5 can for instance be used to turn certain parts of the respiratory system, such as humidifier system, flow generators, heated hoses, or the entire respiratory system on or off. The HMI 5 can be located on any part of the respiratory system such as a respiratory mask, a cuff, a hose, or on any other additional equipment, such as a bed or a pillow, or may even be located in another room. The HMI interface is preferably located near the patient such that it enables the patient to segment their treatment. It may be the case that for some reasons the patient is bed bound and thus has to have the treatment continuously. It may be the case that the patient needs different levels of treatment during the course of the day/night. With the appropriate sensors it will be possible for the controller to determine sleep patterns and adjust the equipment accordingly. It may be the case that patients don't want the hose to be heated continuously the patient may require different temperature settings and these can be adjusted automatically via ambient tracking or can be adjusted with the HMI 5. Another advantage of the HMI in combination with the interconnecting conduit is that the flow generator and or humidifier can be located further away from the patient, and thus noise reduction techniques can be used and thus improving patient comfort. To reduced noise the unit could be located in a cabinet, which may perform a number of different tasks. Firstly it can be used to reduce the noise, and light form disturbing the patient. Secondly the cabinet could be used to improve and stabilize the ambient conditions for the humidifier/flow generator.

The HMI 5 can for instance be used to initiate an alarm function. It is for instance possible that a patient is bed bound and needs help from another person. The HMI 5 could be used to initiate an alarm function on the controller or any other associated piece of equipment. The HMI 5 could be used to reset certain alarm functions with associated pieces of equipment. It may be the case that an alarm function has been tripped, for example over temperature, lack of airflow etc. In the event of an alarm function the HMI can be used to reset and restart the equipment.

The HMI 5 could be used to adjust the operating conditions such as flow pressure, temperature, humidity levels, and if required control the administering of any associated medicines that might be connected to the respiratory system.

The HMI 5 can use the respiratory conduit wiring systems to communicate with associated equipment, or can use wireless technology such as infrared, radio, bluetooth. Usually, the wiring requirements for the HMI 5 control functions will be lower than those needed for the heating wires. The HMI could if required utilize very low voltages such as 5V. Using lower voltages reduces the wire sizes and increases patient safety. The HMI 5 can be mobile allowing medical practitioners operating respiratory system parts from another room. The HMI 5 can receive signals to indicate equipment performance such as temperature, alarm functions, water levels etc.

Figure 16:
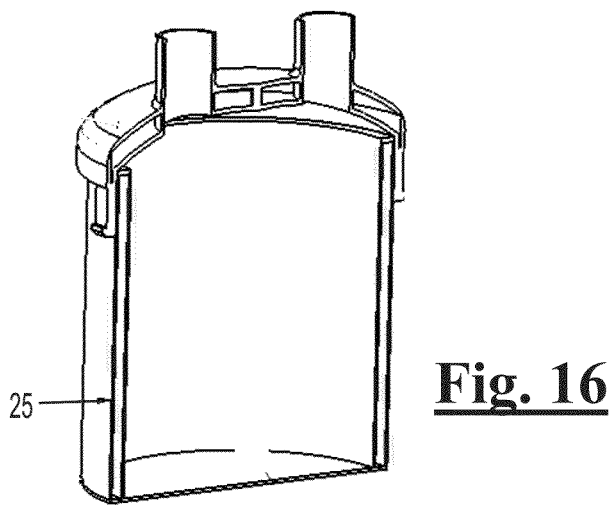
FIG. 16 shows a humidifier chamber of a humidifier system, according to an aspect of the invention, which is thermally insulated from ambient conditions.

FIG. 16 shows a humidifier chamber of a humidifier system. The humidifier chamber is thermally insulated from ambient conditions. The insulation is done with a double walled chamber construction 25 which comprises a cavity which is filled with air, but may be filled with any insulating material such as a foam.

FIGS. 17-20 show different 4 wire circuit that may be used in a conduit according to any aspect of the present invention.

Figure 17:
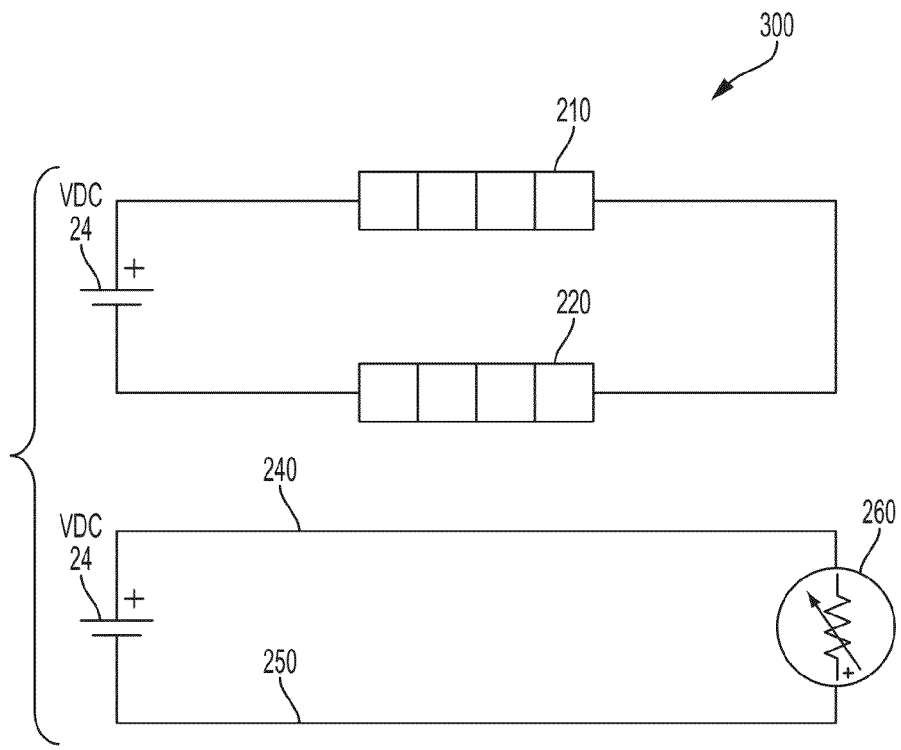
FIGS. 17-20 show different 4-wire circuits that may be used in conduits according to aspects of the invention.

FIG. 17 shows a standard 24 VDC circuit 300. The circuit comprises two heater wires 210 and 220 for heating the breathable gas to be passed to the patient, and two signal wires 240 and 250 provided for transferring the measurements of the at least one sensor. The at least one sensor as shown in FIG. 17 is a thermistor 260, but may be any type of sensor considered suitable by the person skilled in the art. Due to the fact that four wires can be used, the heating circuit and the temperature measuring circuit can operate independently. The circuit shown in FIG. 17 further has the advantage that the sensor may be monitored continuously.

Figure 18:
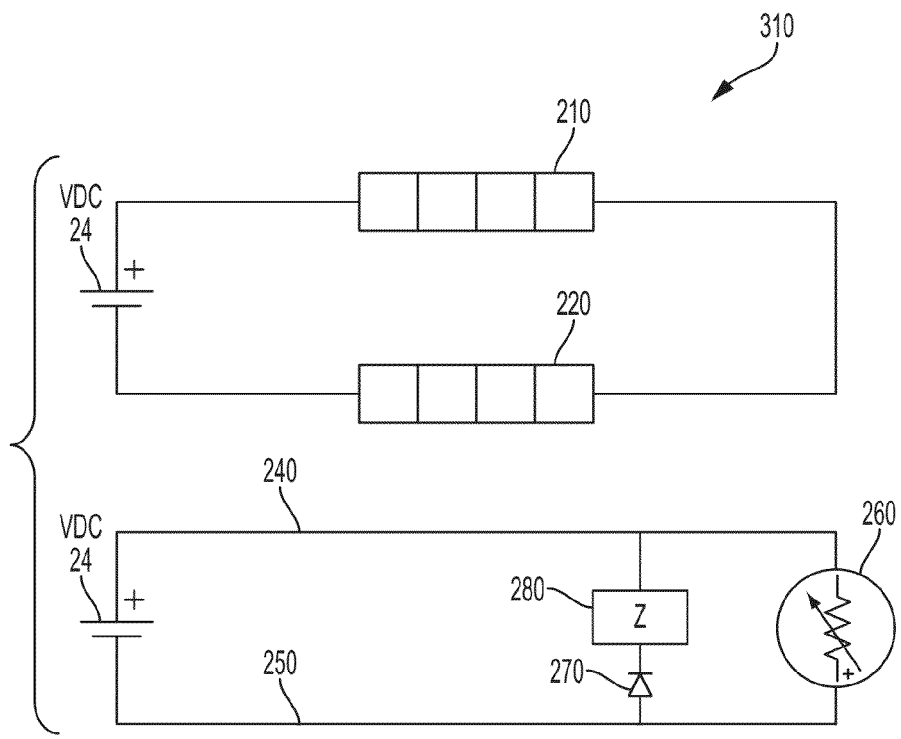

FIG. 18 shows another standard 24 VDC circuit 310. The circuit comprises two heater wires 210 and 220 for heating the breathable gas to be passed to the patient, and two signal wires 240 and 250 provided for transferring the measurements of the at least one sensor. The at least one sensor as shown in FIG. 18 comprises a thermistor 260 as well as sensor 280. A second sensor can for instance be used as a HMI. Due to the fact that four wires can be used the heating circuit and the temperature measuring circuit can be operated independently. The second circuit with the use of a diode 270 can also contain two sensors, either one of which could be a HMI.

Figure 19:
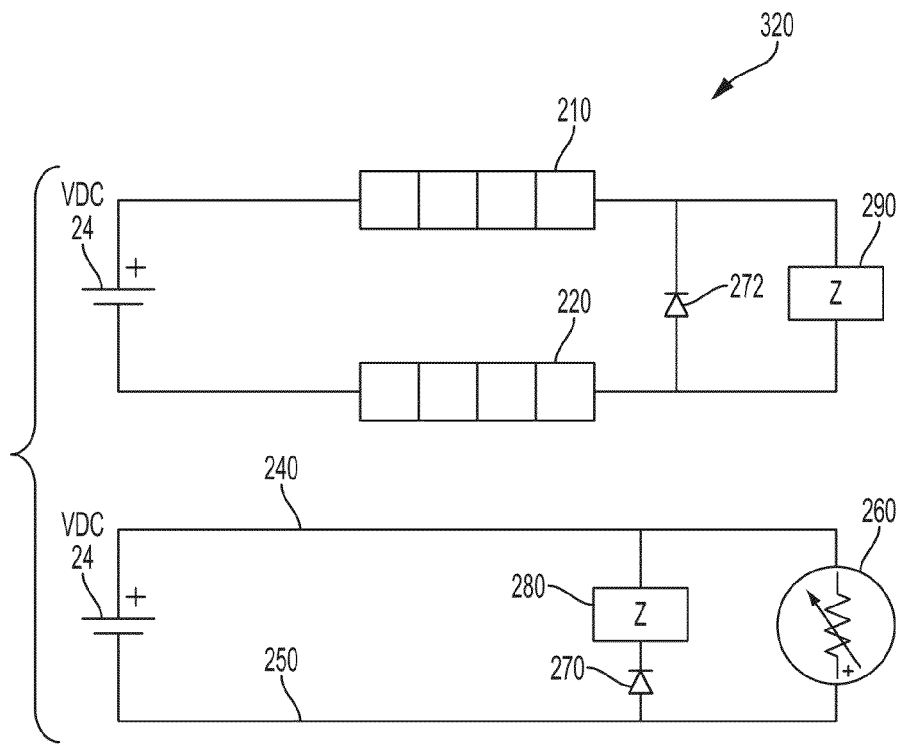

FIG. 19 shows another standard 24 VDC circuit 320. Due to the fact that four wires can be used the heating circuit and the temperature measuring circuit can operate independently. In the heating circuit there is now a diode 272 and an additional sensor 290. The remainder of the circuit is the same as that of FIG. 18.

Figure 20:
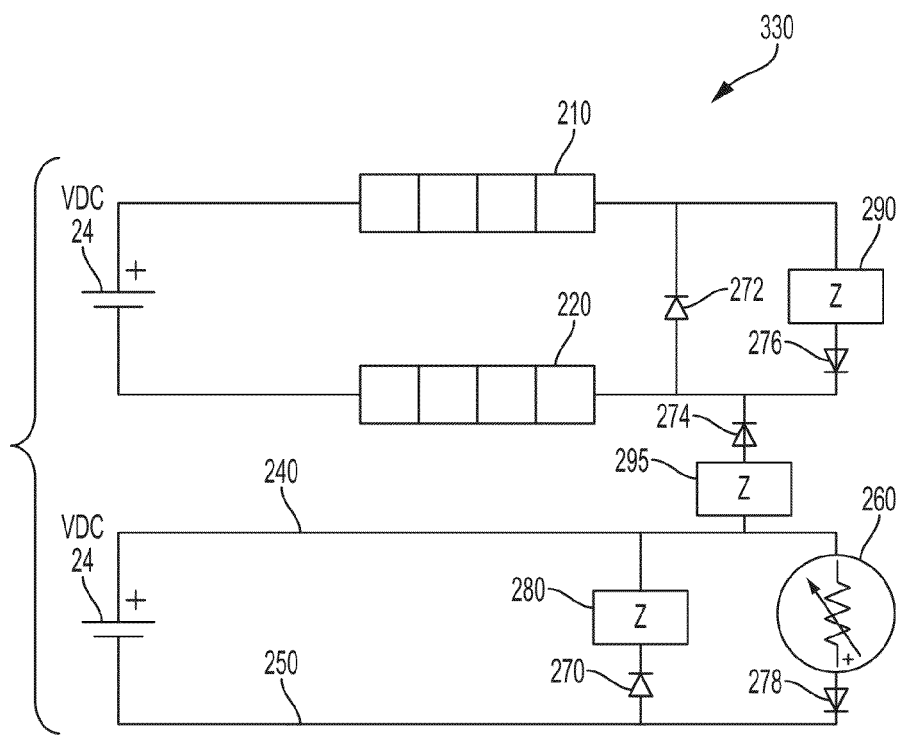

FIG. 20 shows another standard 24 VDC circuit 330. Due to the fact that four wires can be used the heating circuit and the temperature measuring circuit can operate together. In the heating circuit there are now two diodes 272 and 276 and an additional sensor 290, in the second circuit there are now two diodes 270 and 278, and now between the two circuits that is also a diode 274 and a further sensor 295. This shows that using the four wire configuration it is possible to have four sensors.

The invention claimed is:

1. A respiratory system comprising:
   a humidifier system comprising an inlet for taking in a breathable gas and a humidification chamber connected to the inlet for heating and humidifying the breathable gas before delivery to a patient;
   a pre-conditioning system for pre-conditioning the breathable gas before entry into the humidification chamber in a controlled manner;
   a controller for controlling the respiratory system;
   a first dewpoint system for determining the dewpoint of the breathable gas in the inlet and communicating with the controller,
   a patient interface;
   a conduit connectable to the humidifier system and the patient interface for supplying the breathable gas to the patient interface;
   a heating system associated with the conduit for heating the breathable gas delivered from the humidifier system to the patient interface, the heating system comprising a heating element in communication with the controller; and at least one second dewpoint system for determining the dewpoint of the breathable gas in at least one part of the conduit between the humidifier and the patient interface;

wherein the controller is provided for controlling the pre-conditioning system and the heating system associated with the conduit on the basis of dewpoint values determined by the first and second dewpoint systems.

2. The respiratory system according to claim 1, wherein the pre-conditioning system comprises a temperature control system for influencing the temperature of the breathable gas at the inlet before entry into the humidification chamber.

3. The respiratory system according to claim 2, wherein the temperature control system comprises an inlet hose defining said inlet connectable between the flow generator and the inlet of the humidification chamber, and wherein the temperature control system further comprises an inlet heating element associated with the inlet hose provided for heating the breathable gas before entry into the humidification chamber under control of the controller of the respiratory system.

4. The respiratory system according to claim 1, wherein the pre-conditioning system comprises a humidification control system for influencing the humidity of the breathable gas at the inlet before entry into the humidification chamber.

5. The respiratory system according to claim 1, wherein the pre-conditioning system comprises an integrated humidifier of a flow generator for heating and humidifying the breathable gas before entry into the humidification chamber in a controlled manner.

6. The respiratory system according to claim 1, wherein the pre-conditioning system comprises at least one sensor for measuring the temperature and/or humidity of the ambient air.

7. The respiratory system according to claim 1, wherein at least part of the humidifier system is thermally isolated from ambient conditions.

8. The respiratory system according to claim 1, wherein one of the at least one second dewpoint systems is provided for determining the dewpoint of the breathable gas in said conduit on a location near the humidification chamber.

9. The respiratory system according to claim 1, wherein one of the at least one second dewpoint systems is provided for determining the dewpoint of the breathable gas in said conduit on a location near the patient interface.

* * * * *